US012589013B2

(12) United States Patent
    Bourang et al.

(10) Patent No.: US 12,589,013 B2
(45) Date of Patent: Mar. 31, 2026

(54) FULLY CRIMPED STENT FOR TREATING BIFURCATIONS

(71) Applicant: Advanced Bifurcation Systems Inc., Livermore, CA (US)

(72) Inventors: Ashur Bourang, Turlock, CA (US); Henry Bourang, Turlock, CA (US)

(73) Assignee: Advanced Bifurcation Systems Inc., Livermore, CA (US)

( * ) Notice: Subject to any disclaimer, the term of this patent is extended or adjusted under 35 U.S.C. 154(b) by 0 days.

(21) Appl. No.: 17/880,085

(22) Filed: Aug. 3, 2022

(65) Prior Publication Data

US 2023/0040227 A1      Feb. 9, 2023

Related U.S. Application Data

(60) Provisional application No. 63/260,007, filed on Aug. 6, 2021.

(51) Int. Cl.
    *A61F 2/954*      (2013.01)
    *A61F 2/856*      (2013.01)
    (Continued)

(52) U.S. Cl.
    CPC .............. *A61F 2/954* (2013.01); *A61F 2/856* (2013.01); *A61F 2/9522* (2020.05); *A61F 2/958* (2013.01); *A61F 2002/826* (2013.01)

(58) Field of Classification Search
    CPC ........ A61F 2/954; A61F 2/856; A61F 2/9522; A61F 2/958; A61F 2002/826
    See application file for complete search history.

(56) References Cited

U.S. PATENT DOCUMENTS

| | | | |
|---|---|---|---|
| 6,258,099 B1 * | 7/2001 | Mareiro ............ | A61M 25/1002 |
| | | | 606/108 |
| 2002/0120320 A1 * | 8/2002 | Wang ................ | A61M 25/1002 |
| | | | 623/1.11 |

(Continued)

FOREIGN PATENT DOCUMENTS

| | | |
|---|---|---|
| CN | 117915871 | 4/2024 |
| JP | 2024529027 | 8/2024 |
| WO | 2023014830 | 2/2023 |

OTHER PUBLICATIONS

"International Application Serial No. PCT US2022/039328, International Search Report mailed Nov. 1, 2022", 2 pgs.

(Continued)

*Primary Examiner* — Jing Rui Ou
(74) *Attorney, Agent, or Firm* — Schwegman Lundberg & Woessner, P.A.

(57)      ABSTRACT

A stent delivery system for treating a bifurcated vessel includes a first elongate shaft with a first expandable member. A first stent having a side hole is disposed over the first expandable member. A second elongate shaft has a second expandable member. The second elongate shaft is slidably disposed under the proximal end of the first stent and extends out of the side hole. The first stent is fully crimped over a proximal portion and a distal portion of the first expandable member and a proximal portion of the second expandable member so as to prevent axial movement of the first stent relative to the first or second elongate shafts during delivery. Portions of the first or second expandable members may be pillowed to provide a protective barrier that prevents edges of the stent from catching on other objects.

10 Claims, 17 Drawing Sheets

(51) Int. Cl.
| | |
|---|---|
| *A61F 2/95* | (2013.01) |
| *A61F 2/958* | (2013.01) |
| *A61F 2/82* | (2013.01) |

(56) References Cited

U.S. PATENT DOCUMENTS

| | | | |
|---|---|---|---|
| 2003/0074047 A1* | 4/2003 | Richter | A61F 2/958 623/1.11 |
| 2003/0097169 A1* | 5/2003 | Brucker | A61F 2/9662 623/1.11 |
| 2004/0172119 A1* | 9/2004 | Eidenschink | A61F 2/954 623/1.11 |
| 2005/0015108 A1 | 1/2005 | Williams et al. | |
| 2006/0009832 A1* | 1/2006 | Fisher | A61F 2/958 623/1.11 |
| 2008/0154352 A1 | 6/2008 | Goshgarian | |
| 2009/0012601 A1 | 1/2009 | Siu et al. | |
| 2009/0163879 A1* | 6/2009 | Weber | A61M 25/104 606/191 |
| 2009/0171430 A1 | 7/2009 | Baim et al. | |
| 2011/0208286 A1 | 8/2011 | Ta et al. | |
| 2012/0079706 A1 | 4/2012 | Knott et al. | |
| 2014/0100647 A1* | 4/2014 | Bourang | A61F 2/844 623/1.12 |
| 2015/0216691 A1* | 8/2015 | Chuter | A61F 2/958 623/1.11 |
| 2021/0220157 A1 | 7/2021 | Bourang | |
| 2021/0282951 A1 | 9/2021 | Bourang et al. | |

OTHER PUBLICATIONS

"International Application Serial No. PCT/US2022/039328, Written Opinion mailed Nov. 1, 2022", 7 pgs.
"European Application Serial No. 22853876.5, Response to Communication pursuant to Rules 161(1) and 162 EPC filed Sep. 13, 2024", 6 pgs.
"International Application Serial No. PCT/US2022/039328, International Preliminary Report on Patentability mailed Feb. 15, 2024", 9 pgs.
"European Application Serial No. 22853876.5, Extended European Search Report mailed Jun. 4, 2025", 5 pgs.
"Japanese Application Serial No. 2024-506932, Voluntary Amendment filed Aug. 1, 2025", w English claims, 16 pgs.
"European Application Serial No. 22853876.5, Response filed Nov. 19, 2025 to Extended European Search Report mailed Jun. 4, 2025", 29 pgs.

* cited by examiner

FIG. 8C1

FULLY CRIMPED STENT FOR TREATING BIFURCATIONS

CLAIM OF PRIORITY

The present application is a non-provisional of, and claims the benefit of U.S. Provisional Patent Application No. 63/260,007 filed on Aug. 6, 2021; the entire contents of which are incorporated herein by reference.

CROSS-REFERENCE TO RELATED PATENT DOCUMENTS

This patent application is also related to U.S. patent application Ser. No. 17/198,685 filed on Mar. 11, 2021; the entire contents of which are incorporated herein by reference.

BACKGROUND

The present invention relates to medical devices, and more particularly to stenting and treatment of bifurcated vessels. A stent is an implantable scaffold that is typically delivered percutaneously and deployed in a vein, artery, or other tubular body organ for treating an occlusion, stenosis, aneurysm, collapse, dissection, or weakened, diseased, or abnormally dilated vessel or vessel wall. The stent is radially expanded in situ, thereby expanding and/or supporting the vessel wall or body organ wall to reestablish or help maintain patency of the vessel lumen or body cavity. In particular, stents are quite commonly implanted in the coronary, cardiac, pulmonary, neurovascular, peripheral vascular, renal, gastrointestinal, and reproductive systems, and have been successfully implanted in the urinary tract, the bile duct, the esophagus, the tracheo-bronchial tree, and the brain, to reinforce these body organs.

Stents are commonly used to restore patency to a blood vessel thereby allowing blood to flow through a blocked blood vessel. Stents are used to treat stenotic lesions in blood vessels such as coronary arteries that supply oxygen-rich blood to the heart or other parts of the body. Additionally, stents may reduce symptoms such an angina and help to treat myocardial infarctions. Stents are commonly inserted percutaneously by a catheter through an artery such as the femoral artery, radial artery, or brachial artery, and upon reaching the site of deployment, the stent is expanded, re-opening the vessel lumen, and supporting the vessel walls, and the catheter is removed leaving the stent in place.

Conventional stent technology is relatively well developed. Conventional stent designs typically feature a straight tubular, single type cellular structure, configuration, or pattern that is repetitive through translation along the longitudinal axis. In many stent designs, the repeating structure, configuration, or pattern has strut and connecting balloon catheter portions that can impede blood flow at vessels. Further, the configuration of the struts and connecting balloon catheter portions may obstruct the use of post-operative devices to treat vessels.

Therefore, given the challenges of current stent manufacturing processes and stent technology used for treating vascular conditions, a need exists for improved stent delivery systems, methods of delivery and fabrication. At least some of these objectives will be met by the present invention.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in figures of the accompanying drawings.

FIGS. 8A-8C, 8C1 and 8D-8H illustrate a method for manufacturing a fully crimped stent delivery system with pillowed expandable members.

DETAILED DESCRIPTION OF THE INVENTION

Figure 1:
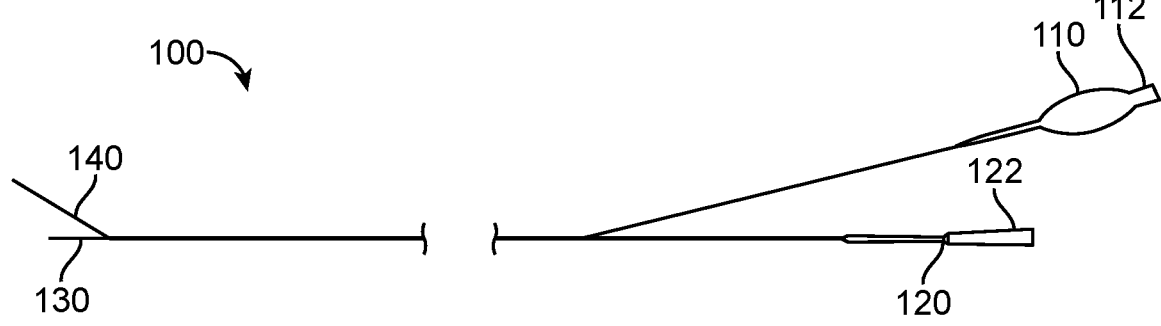
FIG. 1 illustrates a side view of a delivery system having a mother catheter and a daughter catheter.

The present invention generally relates to improving stent delivery systems, delivery methods and manufacturing techniques to make vascular treatments more precise and less likely to cause complications. For example, these systems and methods may be advantageous for mitigating the risk of damaging surrounding tissue during distal advancement through the vessel or for facilitating retention of a prosthesis such as a stent on a delivery system. However, this is not intended to be limiting, and one skill in the art will appreciate that the devices and methods described herein may be used for treating other regions of the body. Examples disclosed herein will focus on stent delivery systems used to treat bifurcated vessels, but this is not intended to be limiting and the examples used herein may be used in other medical treatments or non-medical applications.

Aspects of the subject technology address some of the potential problems of conventional stent delivery systems, which may have limitations and challenges in stent retention when retracting the stent loaded catheter back into an introducer sheath or a guide catheter, as well as during delivery of the stent delivery system through a vessel. For example, a potential challenge of conventional stent delivery systems may occur when the proximal edge of the stent catches on the distal edge of the introducer sheath or guide catheter as the stent is being retracted proximally, causing the stent to become dislodged and/or damaged. Further, upon introduction of the catheter through a vessel, the distal edge of the stent may come into contact with tissue during distal advancement, or a proximal edge of the sent may come into contact with tissue during proximal retraction, thereby causing vessel damage or plaque snow plowing. Tissue damage may occur around curves of a tortuous vessel. In still other situations, a therapeutic agent carried by the stent may be rubbed off or otherwise damaged as the stent proximal or distal edges can scrape against a contact surface during delivery or other use. Examples of stent delivery systems disclosed herein may mitigate the risk of the stent becoming caught on the introducer sheath or guide catheter or causing tissue damage while being introduced or otherwise manipulated. Similarly, examples disclosed herein may also minimize or prevent unwanted damage to a therapeutic agent carried on the stent. These challenges may be mitigated with a stent delivery system that has a "pillowed" region on either side of the stent. The pillowed region is an enlarged protrusion (e.g., bump) that may be a dumbbell shape and may protect an edge on either side or any edge of the stent from becoming dislodged from the catheter or damaging surrounding tissue upon insertion and retraction, as well as protecting therapeutic agents on the stent from being scrapped off or otherwise damaged.

The proximal edge or distal edge of the stent, an edge of the stent, or a therapeutic agent carried by the stent, may be shielded from damage, dislodgement, and tissue damage by use of a radially expandable member. In any examples discussed herein, the radially expandable member may be a balloon. The balloon may have a bump on either end of the stent or adjacent any stent edge that may have a shape memory. The shape memory is induced by heat and pressure over time and the shape may be retained after several cycles on inflation and deflation. Additionally, the balloon may be deflated but still maintains a protective bulge that shields (e.g., a protrusion) due to a shape memory that provides protection from the proximal edge or the distal edge, or any edge of the stent from coming into contact with the sheath or from coming into contact with the tissue or another unwanted contact surface. Thus, the balloon or other radially expandable member may be deflated and re-inflated while still providing the pillowing. The memory may last one or more, two or more, three or more, four or more, five or more, six or more, seven or more, eight or more, nine or more, or greater than ten inflation/deflation cycles before the memory is lost. The radially expandable member in this or any example may be a balloon, or another expandable member used in the deployment of the stent.

In general, the methods disclosed herein may provide protection to the stent or a therapeutic agent or another coating on the stent, by inducing shape memory into the balloon thereby creating a protective protrusion of balloon that protects the stent, therapeutic agent or coating. For example, inducing shape memory may be accomplished by use of inserting the balloon into a mold. The mold may be made from metal, polymer, glass, or ceramic, combinations thereof, or any other material known in the art. In any example, all or a portion of the balloon is disposed in the mold, and a portion of the balloon may be expanded in the mold while another portion is constrained inside or outside of the mold. The mold may be a hand crimper, an iris, or an elongate tubular shaft (e.g., made out of metal, polymer, glass, ceramic, etc.). The balloon may be processed during expansion (e.g. application of heat, pressure, etc.), which induces shape memory into the balloon.

Throughout the present application, reference D represents "distal" and P represents "proximal," and these are relative to the operator of the stent delivery catheter. Thus proximal is closest to the operator and distal is furthest from the operator. The proximal end of the stent delivery catheter is often outside of the human body while the distal end is often inside the patient's body.

Reference will now be made in detail to specific examples of the present disclosure. In the following description, specific details are set forth in order to provide a thorough understanding of the subject matter. It shall be appreciated that any example may be practiced without some or all of these specific details and no specific feature is critical or limiting.

Stent Retention

FIG. 1 shows a side view of a stent delivery system 100 for retaining a stent and delivering the stent to a target treatment area, according to any example. The system comprises a first catheter 120 (e.g., mother catheter or also referred to as a main branch catheter) with a first elongate shaft and a hub 122, and a second catheter 110 (e.g., daughter catheter also referred to as a side branch catheter) with a second elongate shaft and a hub 112. The term "mother" may refer to the catheter, balloon, or the stent in the main branch, while the term "daughter" may refer to the catheter, balloon, or the stent in the side branch. Therefore, the term 'mother' may be interchanged with the term 'main branch,' and the term 'daughter' may be interchanged with the term 'side branch.' The first catheter 120 has a first expandable member, here a balloon 130 (e.g., mother balloon) disposed on a distal portion of the first catheter 120, and the second catheter 110 has a second expandable member, here a balloon 140 (e.g., daughter balloon) disposed on a distal portion of the second catheter 110. A stent (not illustrated) may be disposed over the mother balloon, the daughter balloon, or stents maybe disposed over both balloons. Either catheter may be delivered to a treatment site over a guidewire.

Figure 2A:
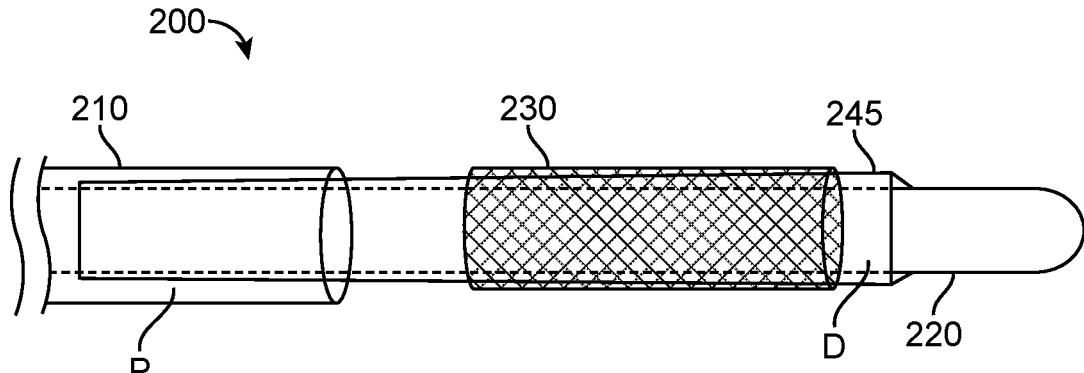
FIG. 2A illustrates a stent delivery system disposed in a guide catheter or introducer sheath.

FIG. 2A shows a sideview of a stent delivery system 200 for retaining a stent 230, indicating the proximal side P and the distal side D of the stent delivery system 200. The system for a stent comprises a delivery catheter 220, an expandable member, here a balloon 245 on a distal portion of a catheter 220, and a stent 230 disposed over the balloon. The balloon 245 has a working length that may match, or may be longer, or shorter than the stent 230 length. The balloon 245 may comprise a proximal and distal shouldered region that is connected to the catheter 220, and the catheter may be slidably disposed through the guide catheter 210 (e.g., sheath) during delivery. An introducer sheath or guide catheter 210 is provided in which the catheter 220 and stent 230 may be retracted proximally therethrough so that the stent is protected by the guide catheter 210 during delivery.

Figure 2B:
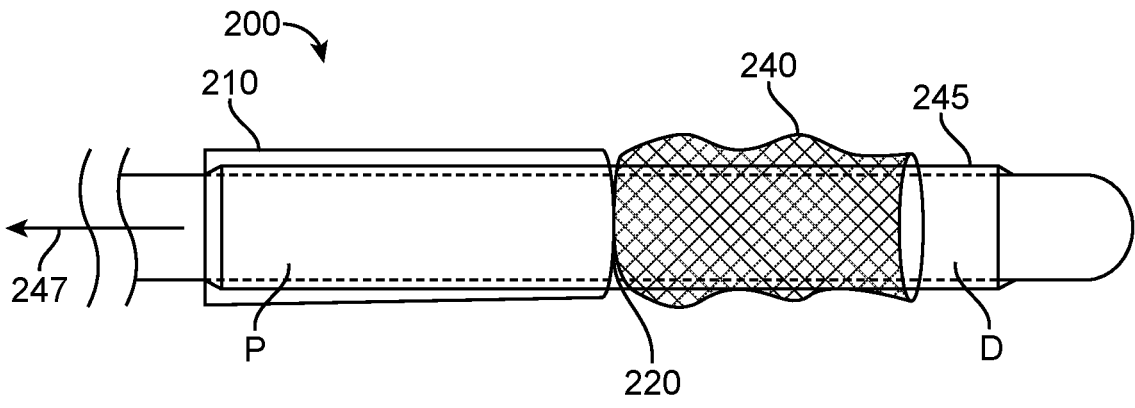
FIG. 2B illustrates a stent edge catching on an edge of the introducer sheath or guide catheter of FIG. 2A.

FIG. 2B shows a side view of the catheter 220, the balloon 245 and the stent 240 in FIG. 2A being retracted proximally as indicated by arrow 247 through the sheath or guide catheter 210. The blunt proximal edge of the stent 240 may come in contact with the distal edge of sheath or guide catheter 210 and induce compressive forces onto the stent 240. The stent may buckle and become deformed, and/or dislodged partially or entirely from the catheter. Additionally, the stent may incur damage that renders it unusable. This can be particularly undesirable when the stent carries a therapeutic agent such as anti-restenosis drugs like paclitaxel or rapamycin or any other drug, since the drug may also be stripped off the stent when the stent catches on the sheath edge.

Figure 2C:
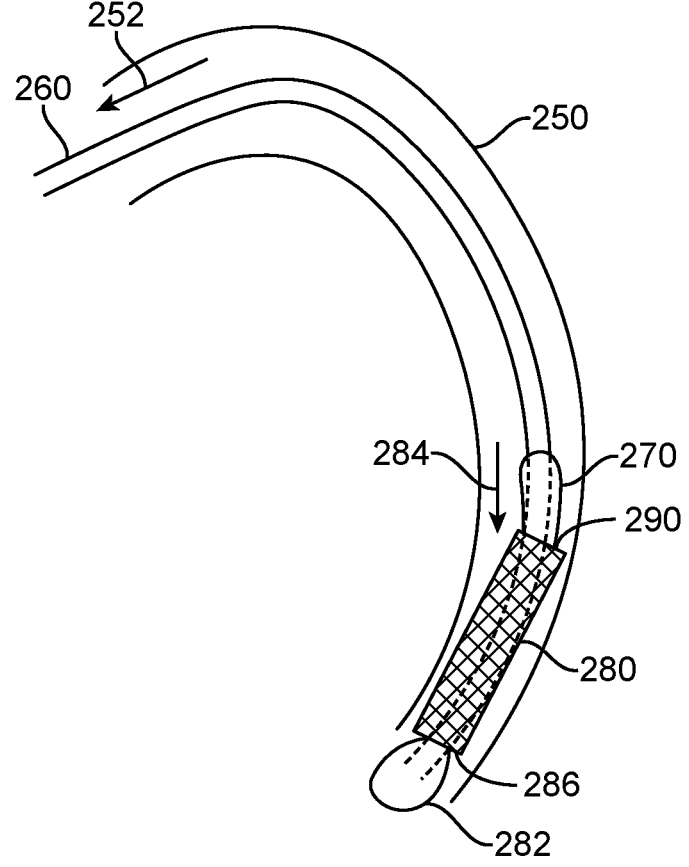
FIG. 2C illustrates a stent edge coming into contact with tissue upon delivery in a vessel.

FIG. 2C shows a side view of the catheter 260, the proximal portion 270 of the balloon and the distal portion 282 of the balloon, and the stent 280 being delivered through a vessel 250. In some examples, the vessel 250 may have an arcuate or tortuous region and the blunt proximal end 290 of the stent 280 may come into contact with the wall of the vessel 250 as the catheter is retracted proximally through the vasculature as shown by arrow 252. The region of contact of the blunt proximal end 290 may cause tissue damage. Damage to the tissue may also occur during distal advancement through the vasculature as shown by arrow 284 in which the distal end 286 of the stent 280 comes into contact with the vessel 250. Contact between the stent edges and the tissue may also damages the stent or cause the stent to eject from the balloon.

Several examples of protecting one or more edges of the stent and forming a protective barrier are disclosed herein.
Shape Memory Formation FIGS. 3A-3D show an example of a process of forming protection on the proximal portion of the balloon.

Figure 3A:
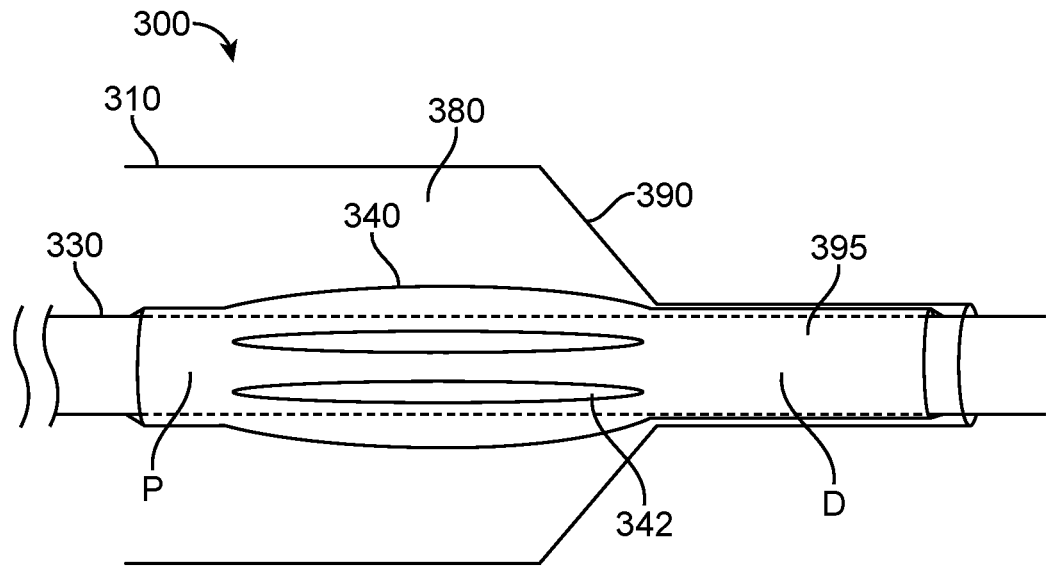
FIG. 3A illustrates a side view of a radially expandable member disposed in a mold.

FIG. 3A shows a side view of a system 300 for forming the balloon to help protect and retain a stent on a stent delivery catheter. The stent delivery system comprises a stent delivery catheter having a first catheter 330, and a folded balloon 340 on the first catheter 330. The balloon 340 may have pleats or folds 342 when the balloon 340 is in a neutral (e.g., unexpanded) state. The balloon is fixedly attached to the first catheter 330. The first catheter 330 and balloon 340 are inserted into a mold 310. The mold 310 may be made from ceramic, glass, polymer, or metal, or combinations thereof, or any other material known in the art. In this or any example, a portion of the balloon 340 may be constrained by the mold 310. The mold 310 comprises a first cavity 380, a second cavity 395, and a transition region such as a taper portion 390 may be disposed therebetween. The first cavity of the mold 310 is cylindrical and the second cavity of the mold 310 is also cylindrical, in which the first cavity 380 has a larger diameter than the second cavity 395. The mold 310 may have the same length as the balloon 340, or a larger length than the balloon 340. A proximal portion of the balloon 340 may be disposed in the first cavity 380, and a distal portion of the balloon 340 may be disposed in the second cavity 395. Additionally, a portion between the proximal portion of the balloon 340 and a distal portion of the balloon 340 may be disposed in the taper portion 390. The distal portion of the balloon 340 is disposed in the second cavity of the mold 310 which is sized to fit closely with the balloon, so the distal portion of the balloon is constrained by the mold and does not allow expansion of the distal portion of balloon 340 (or substantially no expansion).

The first cavity 380 has a diameter that is greater than the folded balloon 340 in its unexpanded state and allows expansion of the proximal portion of the balloon. The first cavity 380 may have a larger diameter than the fully expanded balloon 340, which may allow the balloon 340 to fully expand. Alternatively, the first cavity 380 may have a smaller diameter than the balloon 340 in its fully expanded state, which prevents the balloon 340 from further expansion (e.g., full expansion of the balloon) after the balloon 340 abuts the inside wall of the first cavity 380. The proximal portion of the balloon 340 may expand to create a pillow region. The pillow region creates a protective cover for the edge of the stent during introduction and retraction into and out of the vasculature, as well as providing a protective edge that helps prevent therapeutic agents or other coatings on the stent from being scraped off of the stent. The first cavity 380 is greater than or equal to the length of the pillow region on the proximal portion of the balloon 340. The second cavity 395 has a diameter sized to receive the distal portion of the balloon 340, however it constrains the distal portion of the radially expandable portion and does not allow for expansion when the balloon is heated and pressurized. The second cavity 395 is greater than or equal to the length of the distal portion of the balloon 340.

Figure 3B:
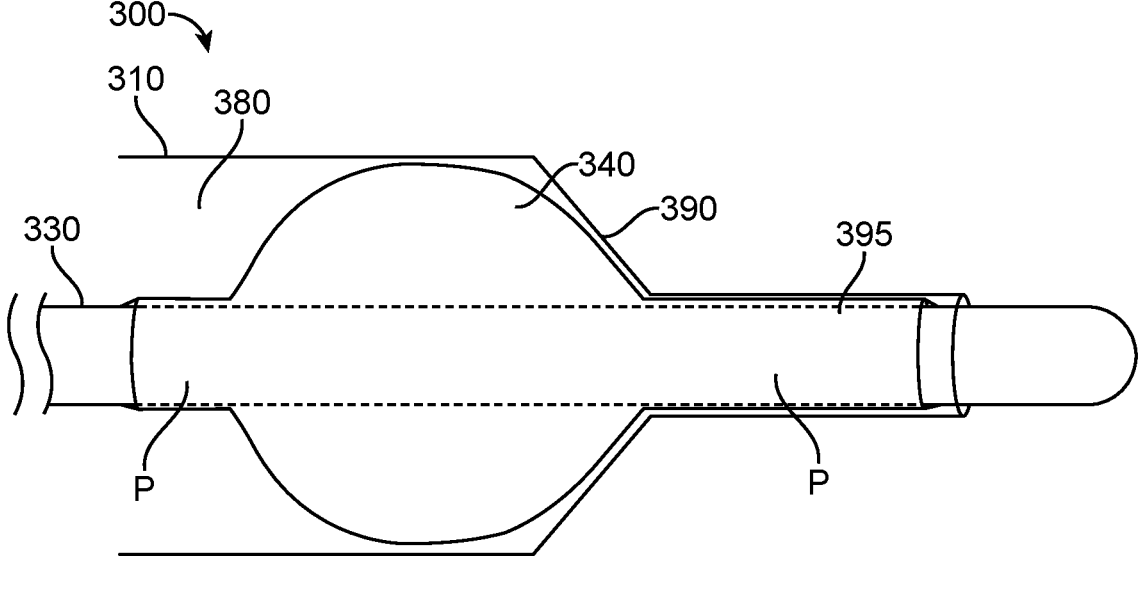
FIG. 3B illustrates a side view of FIG. 3A after radial expansion of the radially expandable member into the mold.

FIG. 3B shows a side view of a stent delivery system 300 in FIG. 3A when the balloon is pressurized. The balloon 340 may be expanded in the mold 310. The expansion of the balloon 340 occurs when heat is applied to the mold 310 and pressure is applied to inflate the balloon 340. The heat, pressure, and dwell time in the mold will be explained below. In one example, a proximal portion of the balloon 340 is expanded in the mold 310, while the distal portion of the balloon 340 is constrained as explained above.

Figures 4A, 4B:
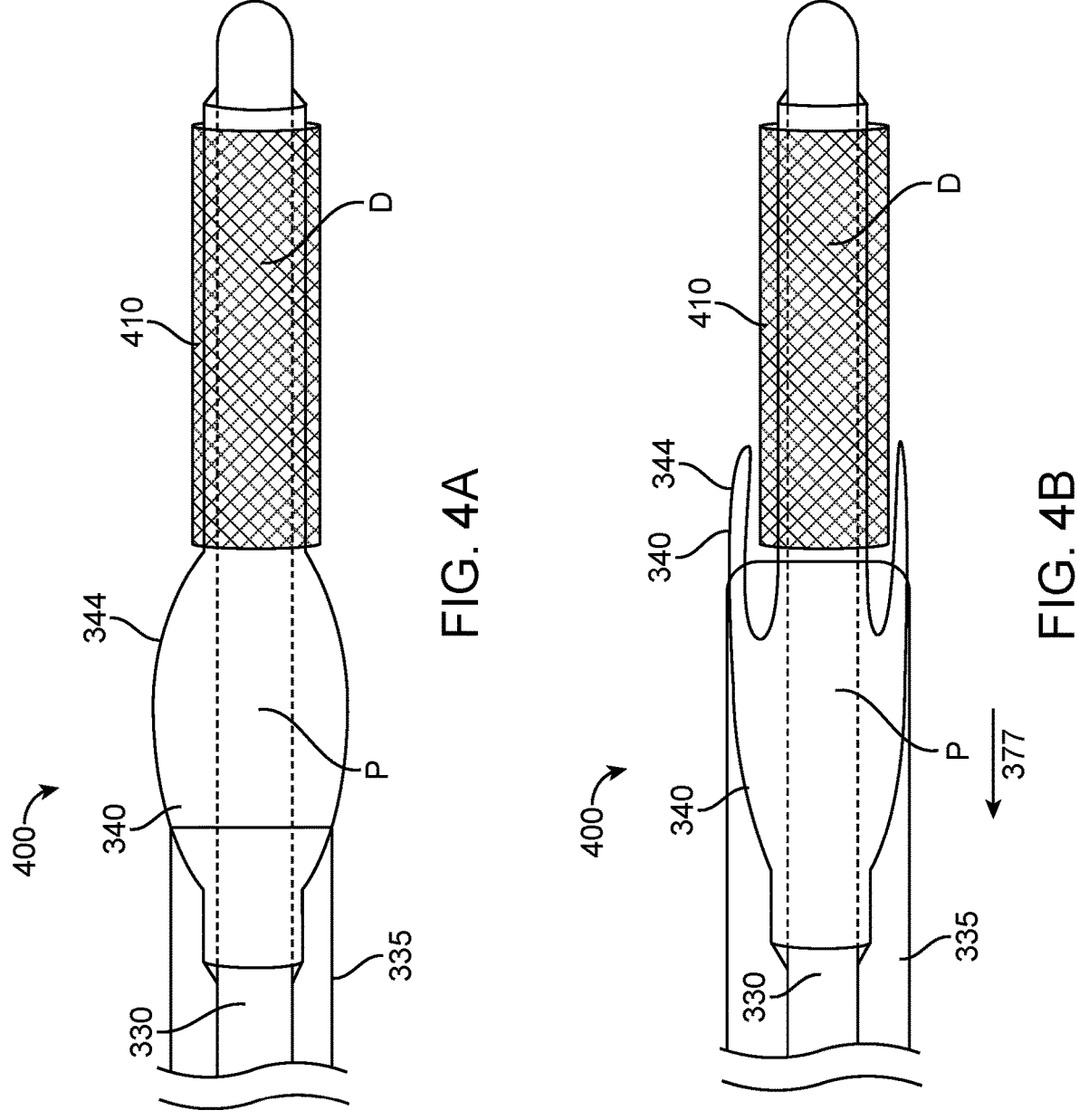
FIG. 4A illustrates a side view of a stent loaded onto a radially expandable member with a pillow formed after processing in the mold.
FIG. 4B illustrates a side view of a pillow protecting the stent from engaging an edge of the sheath.

The entire balloon 340 may experience heat and pressure in the mold 310, however only the proximal portion of the balloon 340 may expand because the distal portion of the balloon 340 may be constrained, and therefore unable to inflate. Additionally, an optional protective sheath 335 as shown in FIG. 4A below, may be applied to a portion of the balloon 340 in the mold to prevent inflation. The constrained portion of the balloon 340 has a smaller diameter than the unconstrained portion of the balloon 340 as shown in FIG. 4A.

In any example, a proximal portion of the balloon 340 may be inflated under heat and pressure to contact the inside wall of the first cavity 380, and a distal portion of the balloon 340 is constrained and so it remains unexpanded. The proximal portion of the balloon 340 may be fully inflated, in which it radially expands to the full diameter of the balloon 340 with or without contacting the inside walls of the first cavity 380. Alternatively, the balloon 340 may be partially inflated in which further expansion of the balloon 340 is prevented upon contacting the inside wall of the first cavity 380. Alternatively, the balloon 340 may be partially expanded such that it does not reach its full diameter or come in contact with the inner surface of the mold wall.

Figure 3C:
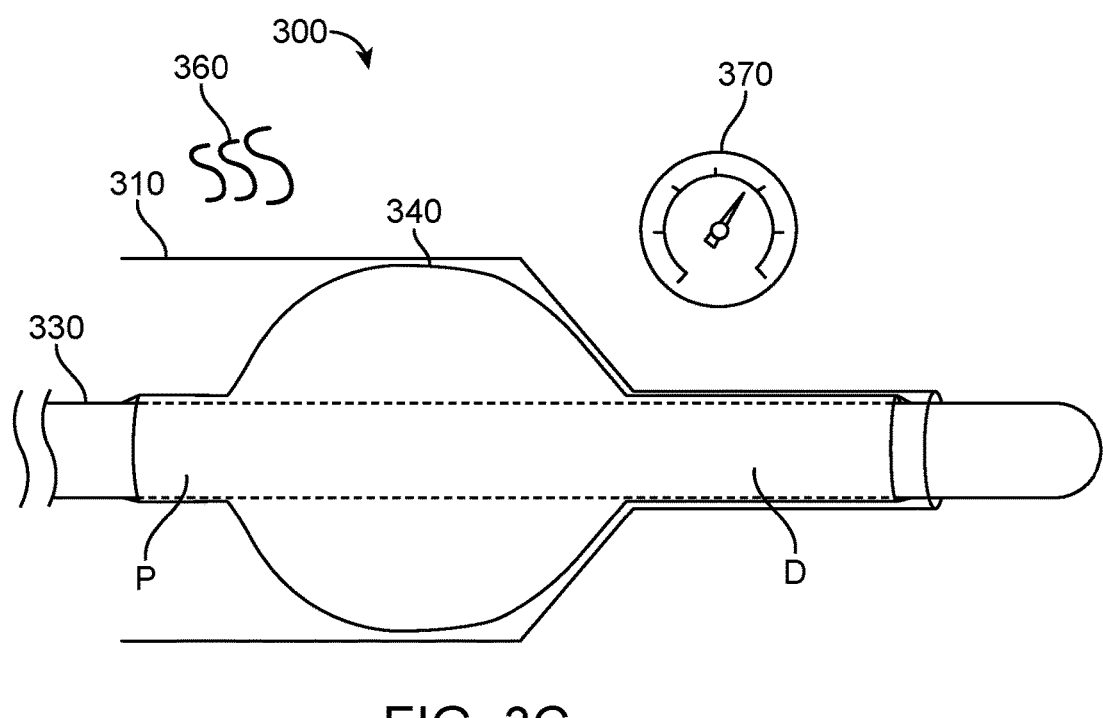
FIG. 3C illustrates a side view of FIG. 3B during processing of the radially expandable member in the mold.

FIG. 3C shows a side view of processing the balloon in FIG. 3B while disposed in the mold. In this example the entire balloon 340 may be disposed in the mold and receives treatment, but only the proximal portion of the balloon 340 expands into contact with the larger proximal diameter of the mold while the distal portion of the balloon 340 does not expand as it is constrained by the mold. The treatment may include adding heat 360, pressure 370, or both for a predetermined time. In any example, the added heat 360, pressure 370, or both, may induce shape memory of the balloon 340. Once a stent is placed on the balloon 340, the shape memory may protect the edges of the stent. The shape memory may create a bump or a dumbbell protruding from the edge of the stent that retains its shape after a series of inflating and deflating the balloon 340. Heat 360, pressure 370, or both are applied for a predetermined time, which will induce shape memory to the balloon 340 in the mold. In any example, the heat 360 may be between 40° C. and 80° C., or between 50° C. and 70° C., or between 55° C. and 65° C., or the heat may be 60° C. In any example, the pressure 370 applied to the balloon may be between 100 psi and 150 psi, or between 110 psi and 140 psi, or between 110 psi and 130 psi, or between 115 psi and 130 psi, or between 120 psi and 125 psi, or between 120 psi or 125 psi. The dwell time may be the amount of time that heat 360 and/or pressure 370 are applied. In any example, the dwell time may be between 15 seconds and 2 minutes, or between 15 seconds and 1 minute, or between 30 seconds and 1 minute, or between 1 minute and 1 minute and 30 seconds, or between 1 minute and 30 seconds and 2 minutes, or the dwell time may be 30 seconds, 45 seconds, 1 minute, 1 minute and 15 seconds, 1 minute and 30 seconds, 1 minute and 45 seconds, or 2 minutes. Any combination or permutation of the ranges of time, temperature, or pressure may be used to process the balloon. Although heat 360 and pressure 370 are applied to the entire radially expandable component, only the expanded proximal portion of the balloon 340 will experience shape memory as the distal portion of the balloon 340 is constrained and remains unexpanded. The shape memory will allow the radially expandable portion 340 to keep the protruded pillowed region, even after it has been completely expanded and completely deflated. The proximal portion of the balloon 340 that experiences shape memory will be larger in diameter than the distal portion of the balloon 340 that was constrained. The shape memory added to the proximal portion of the balloon 340 can last more than 1 cycle, 2 cycles, 3 cycles, 4 cycles, 5 cycles, 6 cycles, 7 cycles, 8 cycles, 9 cycles, or 10 cycles. A cycle is identified by an inflation of the balloon and a deflation of the balloon during preparation or use on a patient.

Figure 3D:
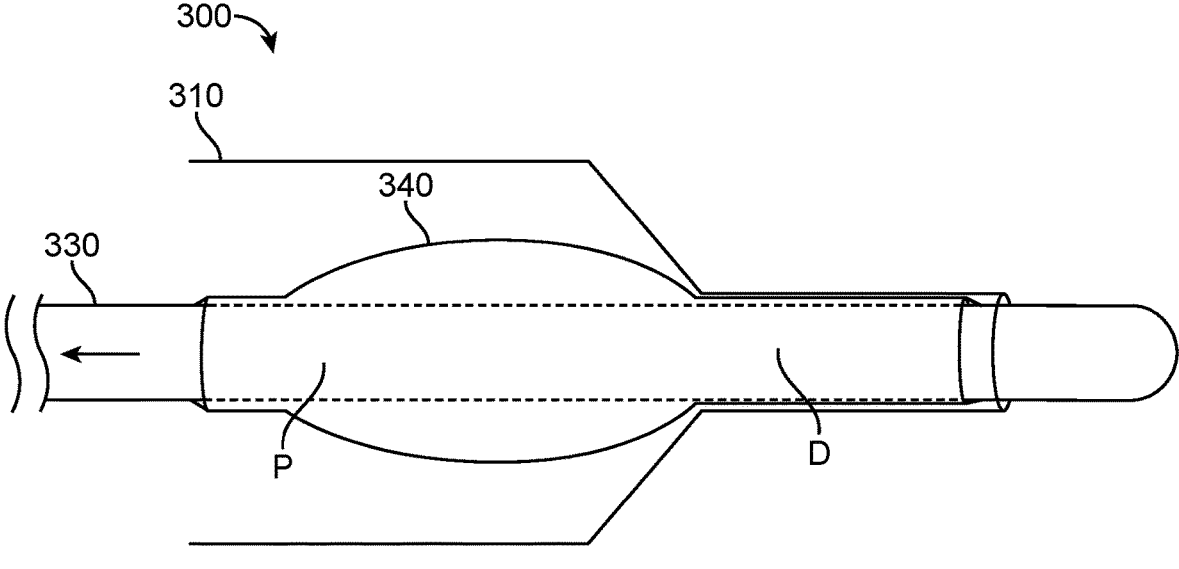
FIG. 3D illustrates a side view of FIG. 3C after collapse of the radially expandable member in the mold.

FIG. 3D shows a side view of deflating the stent delivery system 300. Here, the balloon 340 is completely deflated, but has a shape memory that creates a bump on the proximal portion of the balloon 340. In another example, the balloon 340 is only partially deflated to retain a larger bump on the edge of the stent (not shown) for insertion into the body. The first catheter 330 coupled to the balloon 340 is then removed from the mold 310 and then a stent may be coupled to the delivery catheter.

FIG. 4A shows a sideview of a stent delivery system 400 being loaded onto a stent 410 after forming the shape memory region or regions in the balloon according to any of the examples disclosed herein. In any example, the stent 410 is loaded onto the balloon 340 in such a way that the proximal end of the stent abuts the pillowed or dumbbell shaped protruding portion 344 of the proximal portion of balloon 340. The "pillowing effect" of the proximal portion of the balloon 340 has a larger diameter than the proximal edge of stent 410 thereby creating the shielded edge for the stent. The sheath 335 is disposed over the balloon 340 so that the edge of the sheath passes over the balloon 340 without catching on the stent's edge. The balloon 340 may be collapsed in order to be removed through the sheath 335, or the balloon 340 collapses automatically as it is removed through the sheath 335, however the shape memory remains. This minimizes damage or prevents damages to the proximal edge of the stent.

FIG. 4B shows continued proximal retraction 377 of the delivery catheter and stent 410 in FIG. 4A above, into the sheath 335, in which the protruding region 344 of the balloon 340 protects the proximal blunt edge of the stent 410 as it is drawn further proximally, so the stent 410 does not get caught on the sheath 335 when the delivery catheter is being retracted into the sheath 335. The balloon 340 covers the proximal edge of the stent 410 and prevents it from catching on the sheath 335 which helps to minimize or prevent buckling of the stent or ejection of the stent from the balloon. It also helps or minimizes scraping or other damage to any therapeutic agent carried by the stent or coatings on the stent. Additionally, the proximal edge of the stent 410 is protected from dislodgement or damaging tissue during proximal retraction 377 through the vessel.

Figures 5A, 5B:
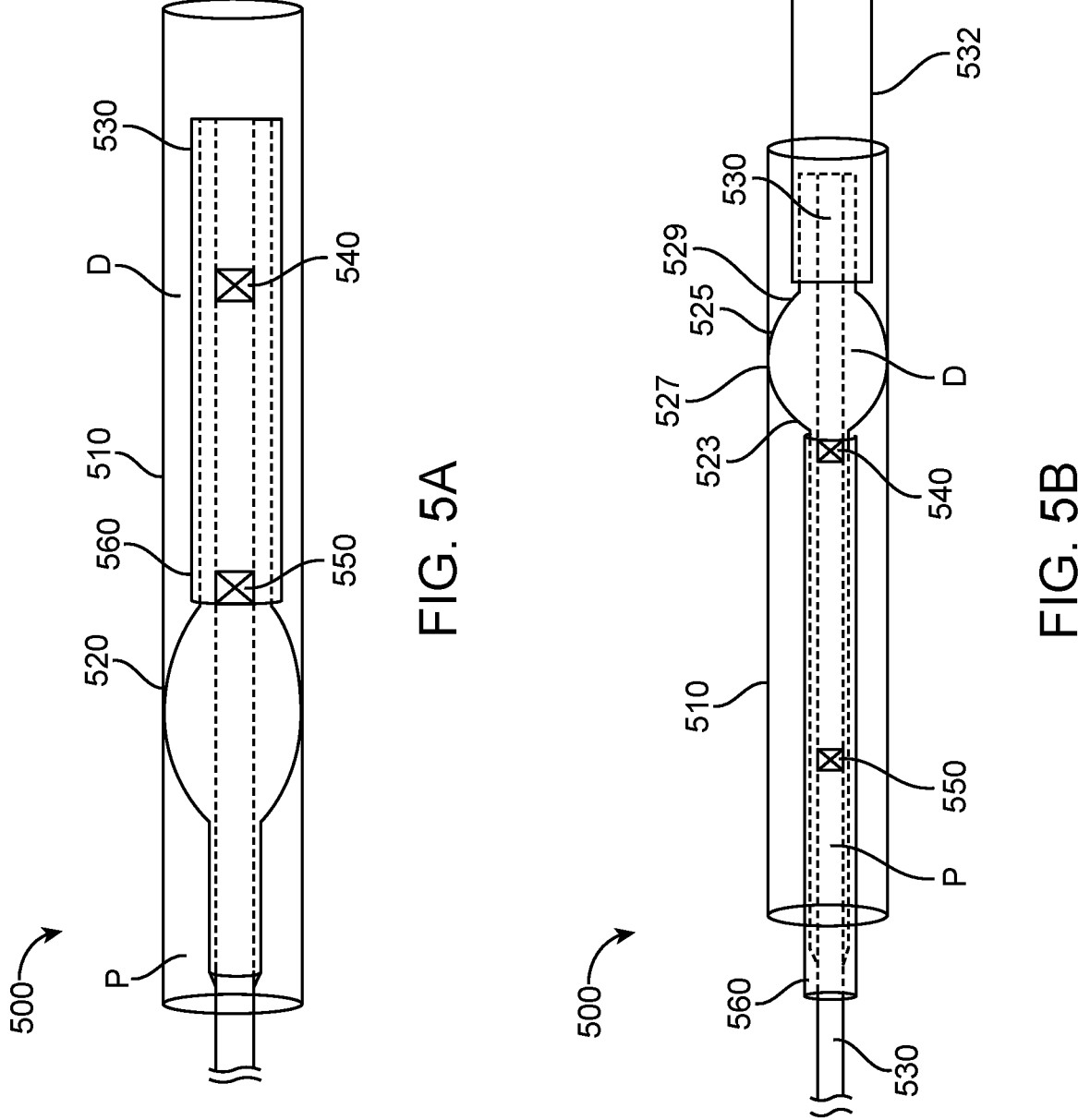
FIG. 5A illustrates a side view of a pillow on the proximal end of the radially expandable member.
FIG. 5B illustrates a side view of a pillow on the distal end of the radially expandable member.

FIG. 5A shows a side view of loading a proximal portion 520 of the balloon into the mold 510 and the protective sheath 560. FIG. 5A is another example of imparting shape memory to a proximal portion 520 of the balloon similar to FIG. 4B above, with the major difference being the mold 510 and protective sheath 560 used during the processing. In the stent delivery system 500, the mold 510 may be an elongate tube. The mold may be made from metal, polymer, or ceramic, combinations thereof, or any other material known in the art. Alternatively, the mold 510 may be the channel formed by the collapsible iris of a crimping system. Alternatively, the mold 510 may be a plastic tube. In the stent delivery system 500, a first catheter 530 has a distal radiopaque marker 540 and a proximal radiopaque marker 550. The distal radiopaque marker 540 and proximal radiopaque 550 markers may provide aid in positioning a stent between each radiopaque markers. The proximal portion 520 of the balloon may have a portion that is constrained, and a portion left unconstrained. In this example, the proximal portion of the balloon is left unconstrained. The distal portion of the balloon may be constrained with a protective sheath 560. The protective sheath 560 may be made from metal, plastic, or any other material known in the art. The protective sheath 560 may restrict a portion of the balloon from expanding. Heat and pressure may be applied for a period of time in order to induce expansion of the unconstrained proximal portion 520 of the balloon using any of the processing parameters previously described above. The proximal portion 520 of the balloon may expand until it reaches the wall of the mold 510. The diameter of the mold 510 may determine the diameter of the pillowed portion of the proximal portion 520 of the balloon. The expansion of the proximal portion 520 induces shape memory into the proximal portion 520. The shape memory may be a pillow as described above in the shape of a bump or a dumbbell protruding on the proximal end of the balloon. The shape memory may withstand several cycles (as previously described above) of inflation and deflation of the proximal portion 520. The stent may be loaded onto the balloon such that the proximal edge of the stent abuts the pillow or at least partially covers the proximal edge of the stent. The shape memory of the proximal portion 520 of the balloon may protect the stent from becoming dislodged or damaged from the retraction of the catheter or causing trauma to tissue as previously described above. Any therapeutic agents carried by the stent or coatings thereon will also be protected by the protruding balloon portion.

FIG. 5B shows another example that is similar to FIG. 5A, however in this example, a distal portion 525 of the balloon is imparted with a shape memory. In the stent delivery system 500, a protective sheath 560 is loaded onto the proximal portion of the first catheter 530 and over the distal portion 525 of the balloon with a small gap of the balloon that remains unconstrained. Two radiopaque markers may be coupled to the first catheter 530. A proximal radiopaque marker 550 and a distal radiopaque marker 540 are placed on a distal portion of the first catheter 530, the proximal radiopaque marker 550 being proximal of the distal radiopaque marker 540. In any example, the protective sheath 560 may constrain a proximal portion 523 of the distal portion 525 of the balloon and leave a distal portion 527 of the distal portion 525 of the balloon unconstrained. Additionally, a constraining sheath 532 may constrain a further distal portion 529 of the distal portion 525 of the balloon from expansion while a more proximal portion of the distal portion 525 of the balloon is unconstrained and allowed to expand and form a pillow (in the gap region between the constrained portions of the balloon), distal of the distal radiopaque marker 540 where the distal edge of the stent will be. Heat may be applied to the mold 510 and pressure may be applied to the distal portion 525 of the balloon to inflate it, in order to induce shape memory to the distal portion 525 of the balloon as described above. The shape memory may be a bump such as a dumbbell shaped protrusion, or a pillow. The shape memory may withstand several cycles of inflation and deflation of the distal portion 525 of the balloon as previously described above. The stent may be loaded onto the balloon such that the distal edge of the stent abuts the distal portion 525 of the balloon or is covered by the protrusion. The shape memory of the distal portion 525 of the balloon may protect the tissue of the vessel upon delivery, protect the distal stent edge, as well as protecting any therapeutic agents carried by the stent or coatings disposed over the stent.

Figures 5C, 5D:
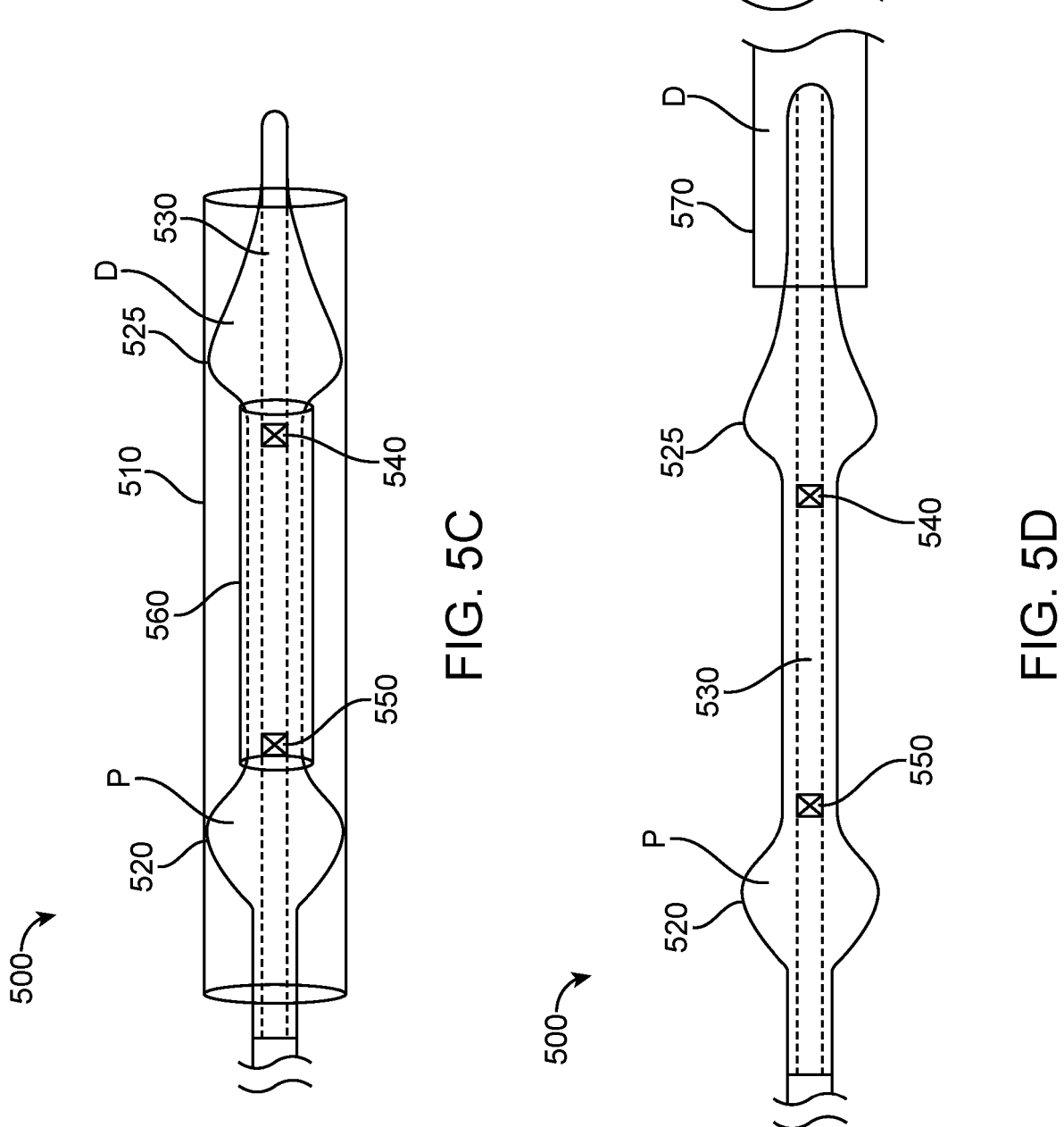
FIG. 5C illustrates a side view of pillows on the proximal and distal ends of the radially expandable member.
FIG. 5D illustrates another view of FIG. 5C after being removed from the mold.

FIG. 5C shows another example of inducing shape memory. In FIG. 5C, shape memory is induced to both a proximal portion 520 of the balloon as described in FIG. 5A above, and a distal portion 525 of the balloon as described in FIG. 5B above. In any example, the pillowed portion of the distal portion 525 of the balloon may be smaller in diameter than the pillowed portion of the proximal portion 520 of the balloon. This may be due to a lower need for pillowing to protect the surrounding tissue. Alternatively, the pillowed portion of proximal portion 520 of the balloon may have a smaller diameter than the pillowed portion of the distal portion 525 of the balloon. This may be due to a lower concern for tissue damage to the surrounding vasculature upon insertion and retraction, and a larger concern for dislodging of the stent upon insertion and retraction. Alternatively, the pillowed regions of the proximal portion 520 of the balloon and the distal portion 525 of the balloon may have the same size diameter. In this or any example, a protective sheath 560 may be placed between the distal portion 525 of the balloon and proximal portion 520 of the balloon to prevent the middle portion from expanding under heat and pressure. The heat, pressure, and dwell time ranges are discussed above. The sheath 560 may be made from any material discussed above. The first catheter 530 may have two or more radiopaque markers on the distal end of the shaft. The distal radiopaque 540 and proximal radiopaque 550 markers may provide aid in alignment of the protective sheath 560 or the stent. The stent may be disposed between each of the radiopaque markers. The distal and proximal portions of the balloon 525 and 520, respectively, may expand to come in contact with the mold 510 when heat and pressure are applied. This forms a dog bone shaped or double dumbbell shaped balloon with protective protrusions on the proximal and distal ends.

In another example, as the protective sheath 560 is loaded into the mold 510, placed in between the distal portion 525 of the balloon and proximal portion 520 of the balloon, the proximal portion 520 or the distal portion 525 of the balloon may be fully expanded or partially expanded. When the distal portion 525 and proximal portion 520 of the balloon are partially expanded, they may not come in contact with the mold 510. Alternatively, the distal portion 525 of the balloon may come in contact with the mold when it is fully expanded, while the proximal portion 520 of the balloon does not when it is partially expanded. Or on the contrary, the proximal potion 520 of the balloon may come in contact with the mold 510 when it is fully expanded, while the distal portion 525 of the balloon does not when it is partially expanded. Whether the distal or proximal portions 525 and 520 of the balloon are fully or partially expanded may depend on the desired diameter size of the distal or proximal portions. For example, if a large proximal portion 520 is desired and a smaller distal portion 525 is desired, the proximal portion 520 may be fully expanded and the distal portion 525 may be partially expanded. In any example, the distal and proximal portions 525 and 520 of the balloon may expand at the same time. Alternatively, the proximal portion may expand before the distal portion. Alternatively, the distal portion may expand before the proximal portion.

FIG. 5D shows an example once the balloon has been removed from the mold 510 and the protective sheath 560 has been removed. Shape memory is induced to the proximal portion 520 and the distal portion 525 of the balloon and may survive a series of balloon inflations and deflations as discussed above. After the shape memory is induced, the stent may be loaded onto the first catheter 530. The stent may be placed between the distal radiopaque 540 and proximal radiopaque 550 markers and disposed over the balloon. A sheath 570 may be inserted onto the balloon.

Figure 5E:
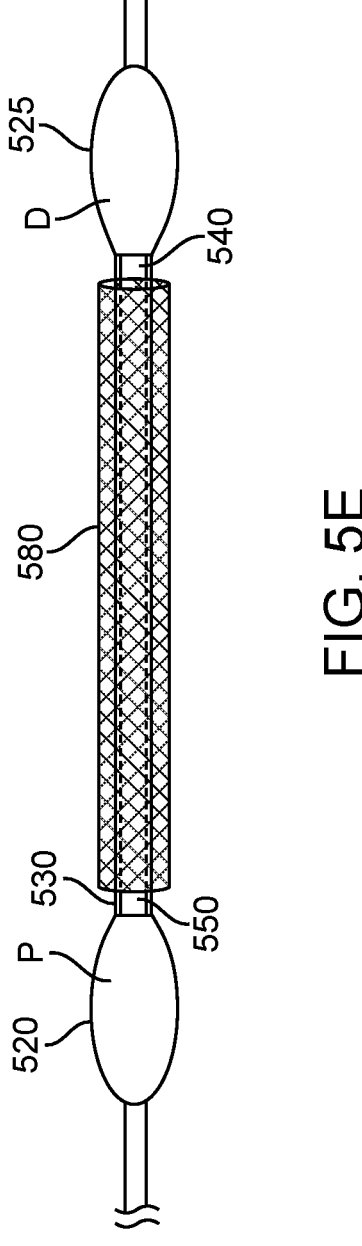
FIG. 5E illustrates a side view of a stent loaded onto a first catheter having proximal and distal pillows.

FIG. 5E shows an example once a stent 580 has been loaded onto the first catheter 530 with the pillowed portion of the proximal portion 520 and the distal portion 525 of the balloon. The stent 580 has been placed in between the proximal radiopaque 550 and distal radiopaque 540 markers.

Combined Stent Crimping and Shape Memory Formation

FIG. 6A-6F show different steps of crimping a stent 610 as it loads over a balloon 620 attached to a distal end of a first catheter 630 for delivery using delivery system 600.

Figures 6A, 6B:
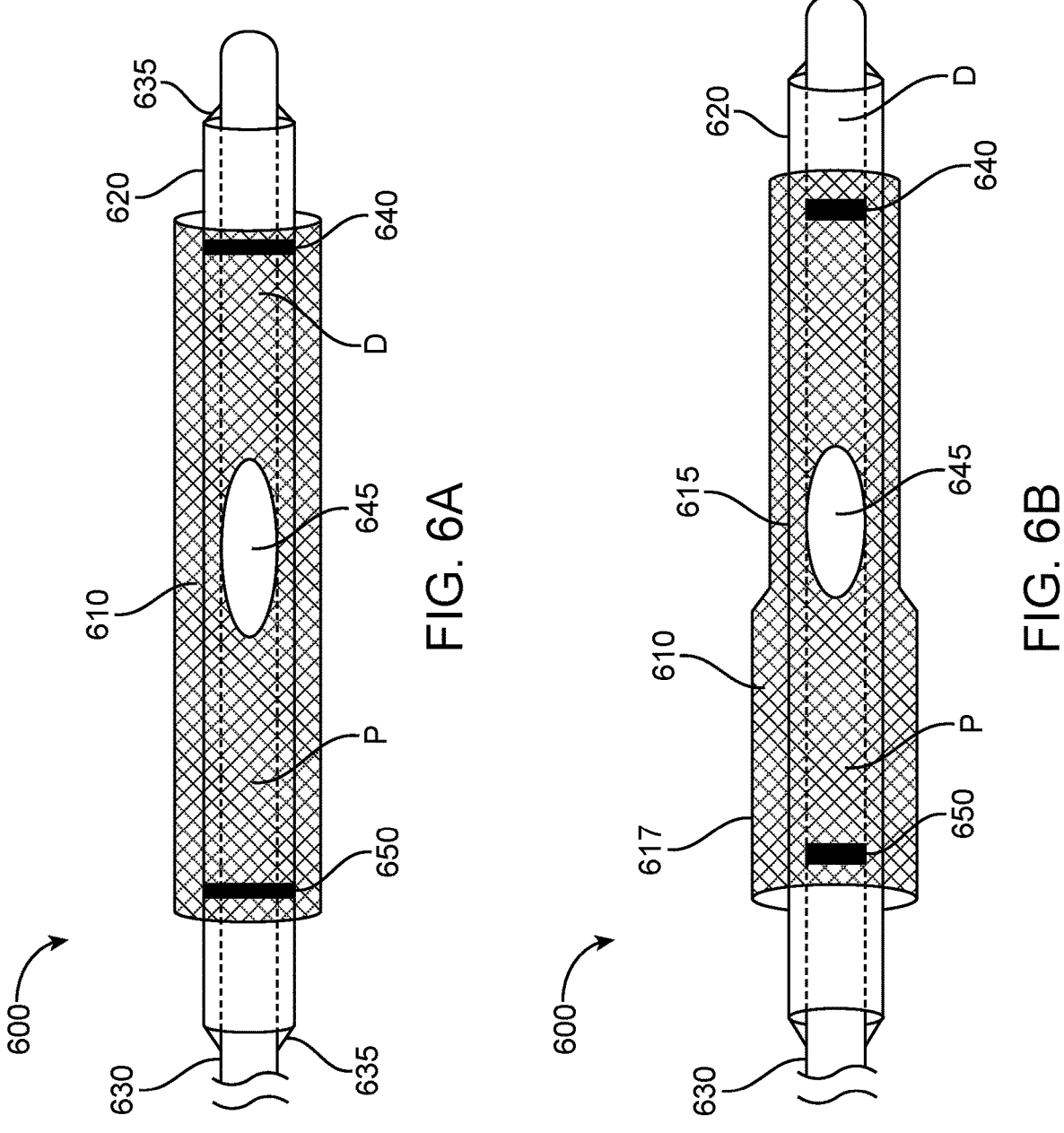
FIG. 6A illustrates a distal portion of another stent delivery system.
FIG. 6B illustrates the stent of FIG. 6A partially crimped to the delivery system.

FIG. 6A shows a system 600 of crimping the stent 610 and expanding the balloon 620 to form one or more of the pillowed regions previously described above. In FIG. 6A, the stent 610 is loaded over the balloon 620 that is attached to a distal end of the first catheter 630 for delivery. The working length of the balloon 620 matches the length of the stent 610 while the balloon shoulders 635 may extend slightly beyond the stent. In some examples, the balloon 620 may be longer than the stent 610 and may extend past the stent 610 on either side. The stent 610 may have a side hole 645, or in some examples where a side hole is used, the space between struts on a stent may be used as the side hole. The first catheter 630 may have two or more radiopaque markers that may aid in the stent alignment over the balloon 620. In this example, there are two radiopaque markers; a distal radiopaque marker 640 and a proximal radiopaque marker 650 that is more proximal than the distal radiopaque marker 640. Both of the markers may be on a distal portion of the first catheter.

In FIG. 6B, a first partial crimp may be applied to a distal portion 615 of the stent 610. The partial crimp provides alignment of the stent onto the balloon 620 and prevents longitudinal movement of the stent 610 so that the stent remains disposed between the radiopaque markers 640, 650. In this or any example, the distal crimp may extend from the distal-most end of the stent up to the side hole 645 or any portion thereof. In any example, the proximal portion 617 of the stent 610 may remain uncrimped. The distal crimp of the distal portion 615 may aid in the alignment between the distal radiopaque marker 640 and the proximal radiopaque marker 650 by holding the stent in position. The distal crimp may be made by a light finger or hand crimp or with any other crimping tool. Alternatively, the distal crimp may be made by inserting the system 600 into a crimping iris that applies pressure and heat for a given time. A protective covering may be applied to the proximal portion 617 of the stent 610 in order to prevent expansion. Alternatively, or additionally, the proximal portion 617 is not inserted into the iris to be crimped.

Figures 6C, 6D:
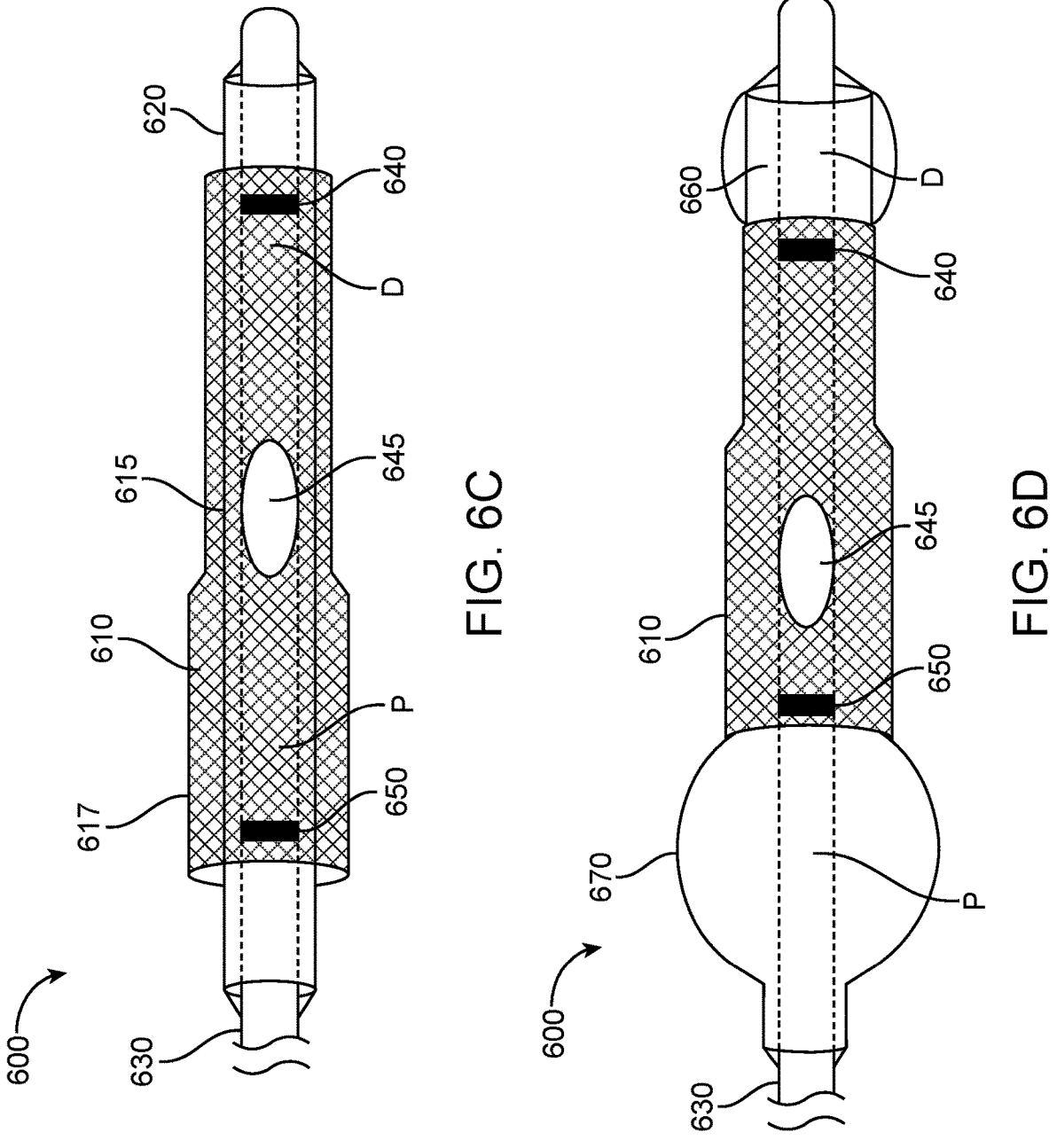
FIG. 6C illustrates the stent of FIG. 6B further crimped to the delivery system.
FIG. 6D illustrates pillowing of the radially expandable member in the stent delivery system of FIG. 6C.

In FIG. 6C, a full crimp is applied to system 600 that causes the stent 610 to embed into the balloon 620. The full crimp may be applied to the distal portion 615, the same portion that was partially crimped the previous step. The full crimp embeds the stent 610 into the balloon 620 and prevents movement or dislodgement of the stent 610. The full crimp may impart some shape memory into the distal portion 615 as heat and pressure is applied for a period of time (refer to operating parameters discussed above), however full expansion may not occur as the dwell time is relatively short in order to crimp the stent. The embedding of the stent into the balloon prevents any longitudinal movement of the stent 610 relative to the balloon 620. Additionally, the full crimp eliminates movement during delivery through a vessel and routine handling and manipulation of the device. A protective covering may be applied to the proximal portion 617 of the stent 610 in order to prevent expansion. Alternatively, or additionally, the proximal portion 617 may not be inserted into the iris to be crimped.

Figures 6E, 6F:
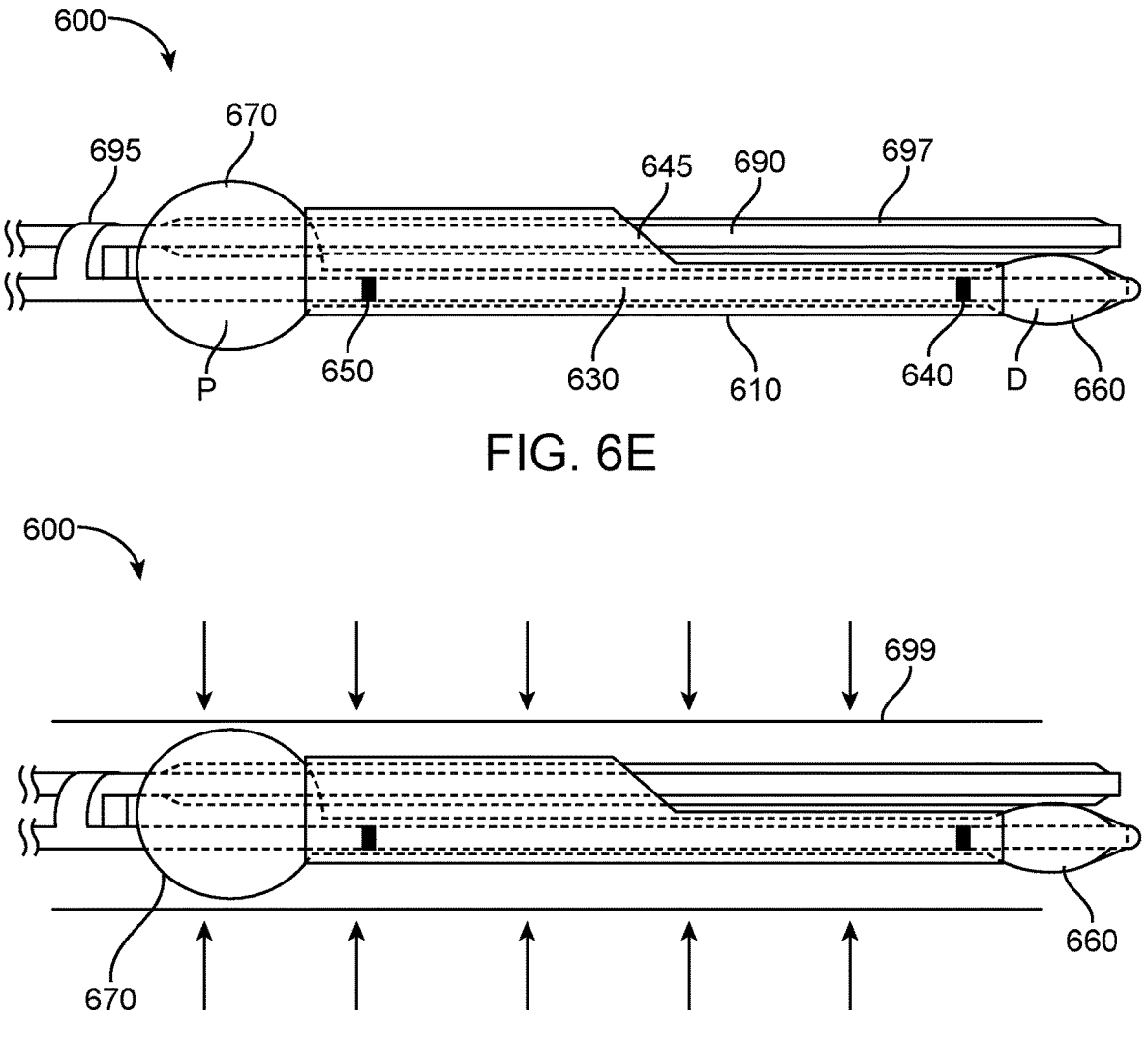
FIG. 6E illustrates the insertion of a second catheter through the stent in FIG. 6D prior to additional stent crimping.
FIG. 6F illustrates the side view of FIG. 6E inserted into a mold for additional crimping.

FIG. 6D is the system of FIG. 6C, in which the system 600 is inserted into a mold (as described above), heat and pressure are applied for a dwell time to form a shape memory. The mold may be any of the materials or shapes discussed herein. The heat is applied to the mold and pressure is applied to the balloon, in response a portion of the balloon partially inflates to form a protrusion such as the dumbbell shape illustrated. This may cause a proximal portion 670 of the balloon to expand as illustrated. Alternatively, this may cause a distal portion 660 of the balloon to expand. In this example, the heat in the mold and pressure in the balloon, causes the proximal 670 and distal portions 660 of the balloon to become pressurized and expand. The proximal portion 670 may be larger in diameter than the distal portion 660 (FIG. 6D shows the distal pillow having a small diameter but is large enough to protrude and form a protective barrier for the distal edge of the stent 610. FIG. 6E or FIG. 6F show the proximal and distal pillows more clearly). Alternatively, the distal portion 660 may be larger in diameter than a proximal portion 670. Alternatively, the distal portion 660 and the proximal portion 670 may have the same diameter. The heat, pressure, and dwell time that imparts a shape memory may create a bump on the balloon which protrudes to cover the proximal or distal ends, or both ends of the stent 610. Alternatively, the bump may be bulbous or dumbbell in shape. The bump may be maintained even after several cycles of inflating and deflating the balloon.

FIG. 6E is a 90° rotated side view of FIG. 6D, with the side hole at the top of the stent 610. A second catheter 690 (e.g., daughter catheter or side branch catheter) is inserted into the side hole 645. The second catheter 690 may contain a second balloon 697. In some examples, the second catheter may contain a second stent (not illustrated) disposed over the second balloon 697. The first catheter may have a hollow exchange port tube 695 that aids in the alignment of the second catheter 690 with the side hole 645 and couples the two catheters together. The hollow exchange port 695 may be made out of glass, plastic, rubber, or any suitable combination thereof. In this example, the second catheter 690 has a distal end that is advanced through the hollow exchange port tube 695 and through the proximal end of the uncrimped proximal portion of stent 610 before exiting out of an optional side hole 645. The insertion of the second catheter 690 through the side hole 645 of the stent 610 may cause an overlap between the first catheter 630 and the second catheter 690. The second catheter 690 may be introduced through the stent 610 through an existing aperture between adjacent struts in the sidewall of the stent 610, or a separate side hole may be formed in the stent.

FIG. 6F shows the system 600 of FIG. 6E inserted into a protective tube 699 which can then be crimped with a crimping machine or crimping tool. Optional heat and pressure may be applied to the balloons during crimping. The heat and pressure applied to the system as discussed above helps embed the stent into the balloon over the working length of the balloon on both the first catheter 630 (e.g., mother catheter) and the second catheter 690 (e.g., daughter catheter). The distal region 660 and the proximal region 670 may experience a reduction in diameter as they will be reduced in size, however the dumbbell shape will remain due to the shape memory imparted to these regions of the balloon. The various vertical arrows illustrate the compression force and movement applied by a crimping machine or crimping tool that crimps the system 600 together.

Fully Crimped Stent

Figure 7:
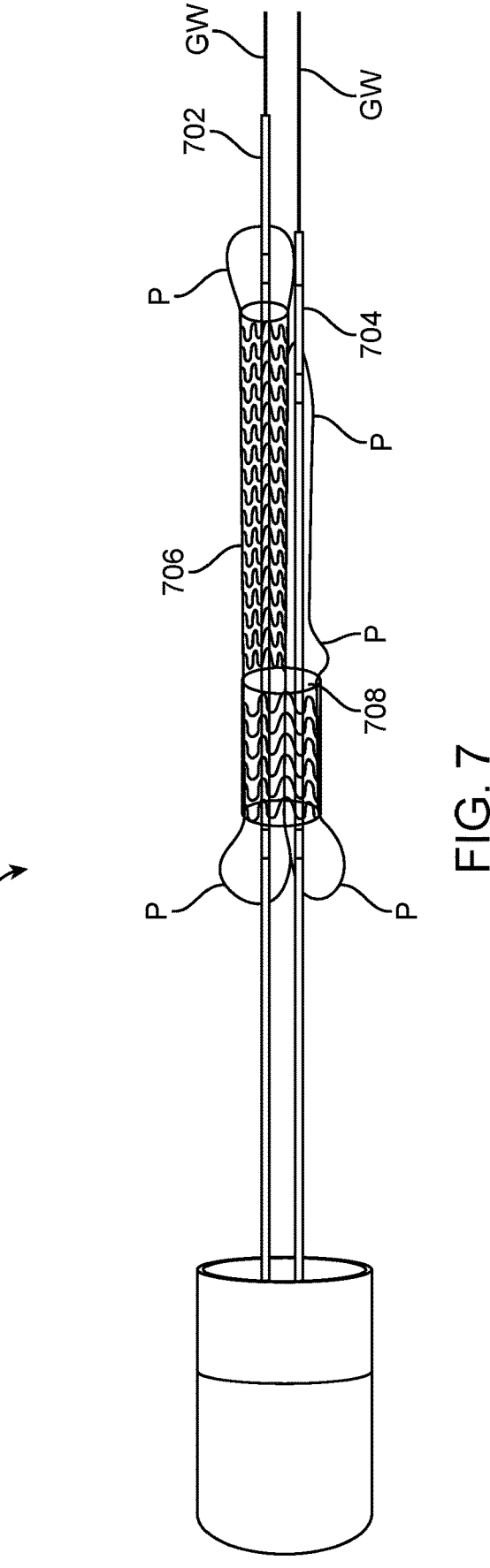
FIG. 7 illustrates an example of a fully crimped stent delivery system.

FIG. 7 shows an example of a fully crimped stent delivery system 700 which may be used to treat bifurcated vessels. Here, the stent delivery system includes two catheters, a mother (or main branch) catheter 702 having an elongate shaft with a proximal end and a distal end, and an expandable member such as a balloon on the distal end of the elongate shaft. The second catheter is a daughter (or side branch) catheter 704 also having an elongate shaft with a proximal end and a distal end, and an expandable member such as a balloon on the distal end of the respective elongate shaft. A mother stent (or main branch stent) 706 is disposed over the mother expandable member and the proximal and distal ends of the mother stent are marked with radiopaque markers on the mother elongate shaft adjacent the proximal and distal ends of the mother stent.

The mother stent has a side wall with a side hole 708 extending therethrough. The stent geometry may be any of the stent geometries disclosed herein or otherwise known in the art. The stent may be self-expanding or balloon expandable.

The daughter catheter is disposed under a proximal portion of the mother stent and exits out of the mother stent side hole 708 so that a portion of the daughter catheter extends along an outer surface of the stent. A radiopaque marker is used to mark the proximal end of the mother stent on the daughter elongate shaft and a distal radiopaque marker marks the distal end of the daughter expandable member.

In this example, the mother stent is fully crimped to both the mother expandable member and the daughter expandable member, thus the stent will not axially move relative to either mother or daughter elongate shafts during delivery of the stent delivery system through a patient's vasculature toward the treatment region in the bifurcated vessel. Additionally, both catheters are stationary relative to one another and the mother stent. Thus, when both catheters are delivered concurrently toward the bifurcation and once the mother catheter is positioned so that the side hole is adjacent the ostia to the side branch (or daughter vessel) of the bifurcation, the daughter catheter may be partially inflated to radially expand the daughter balloon. This creates a small gap between a proximal portion of the mother stent and the daughter balloon which then allows axial movement of the daughter catheter relative to the mother catheter so the daughter catheter may be positioned correctly in the daughter vessel of the bifurcation. Optionally, the mother expandable member may be inflated before the daughter expandable member to create the gap and allow movement of the daughter catheter. Once both mother and daughter catheters are positioned correctly at the bifurcation, the mother catheter may be fully inflated to expand the mother expandable member which correspondingly expands the full length of the mother stent into the treatment region, here a stenotic lesion at the bifurcation or a dissection in the vessel wall. The side hole will align with the ostia to the daughter catheter. The mother and daughter catheters may be simultaneously inflated (kissing balloons) to ensure that the stent is expanded to conform with and engage the native vessel walls. Once the procedure is complete, both balloons may be deflated and the delivery system removed from the patient.

Optionally, a second stent (a daughter stent, not shown) may be disposed over the daughter expandable member and when the daughter catheter is fully expanded, the second stent may be deployed in the daughter vessel. The daughter catheter may be axially aligned relative to the mother catheter so that the proximal end of the daughter stent is adjacent or abutted with the side hole in the mother stent.

Optional guidewires GW (shown in FIG. 7) may be used to help deliver both catheters and thus both catheters may have a guidewire lumen. Also, optionally, the delivery system may be advanced through a guide sheath or introducer catheter if desired.

As previously discussed, in certain situations the proximal edge of the stent, or the distal edge of the stent, or the edge of the side hole can get caught on the distal-most edge of the guide sheath during proximal retraction of the delivery system into the guide sheath, or on the vessel walls during distal or proximal advancement of the delivery system through the vessel. Therefore, in order to avoid this, the proximal end of the mother expandable member, the proximal end of the daughter expandable member, the distal end of the mother expandable member, or an intermediate portion of either or both the mother and daughter expandable members adjacent the side hole may be pillowed P in order to form a raised barrier that will provide a protective barrier to the respective edge of the stent. Thus, a pillowed proximal end of the mother or daughter expandable member provides a protective barrier that will protect and prevent the proximal edge of the mother stent from catching on anything. A pillowed distal end of the mother catheter or daughter catheter will provide a protective barrier that will protect and prevent the distal edge of the mother stent from catching on anything. And similarly, pillowing of the intermediate portion of the mother or daughter expandable members will provide a protective barrier that will protect and prevent the edges of the side hole from catching on anything. The intermediate portion of the mother or daughter expandable member is disposed between the proximal and distal ends of the respective expandable member. The pillowing, sometimes also referred to as a dumbbell or protrusion herein may be formed using any of the manufacturing techniques disclosed herein or otherwise known in the art.

In the example where a daughter stent is disposed over the daughter expandable member, the distal end of the daughter balloon may also be pillowed in order to provide a protective barrier that protects and helps prevent the distal edge of the daughter stent from catching on anything.

Figure 7A:
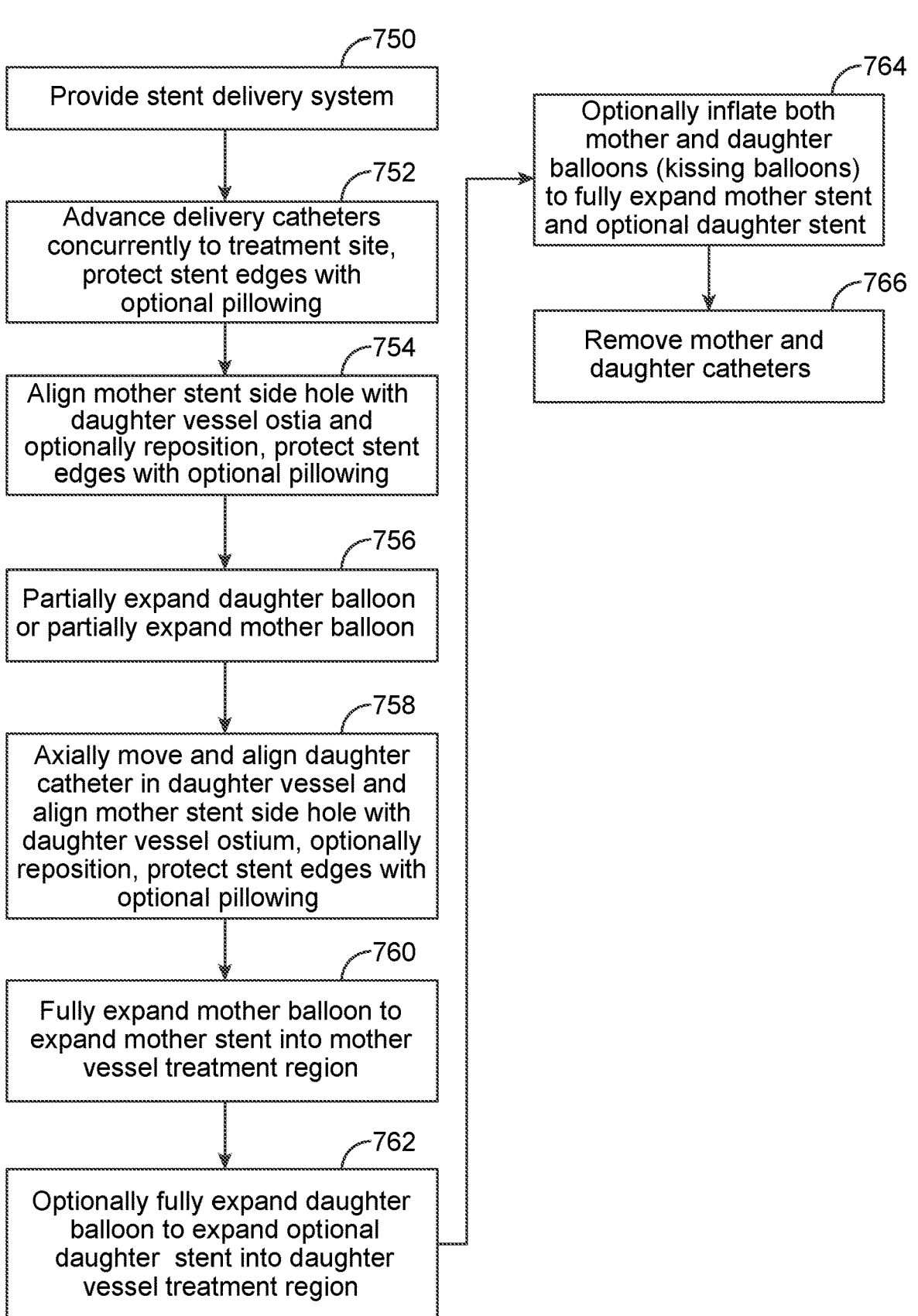
FIG. 7A shows a flowchart illustrating an example of a method of delivering the system in FIG. 7 to a treatment site.

FIG. 7A shows a flowchart illustrating an example of a method of delivering the stent delivery system in FIG. 7 to a treatment area.

The method may use any of the stent delivery systems described herein, 750. The stent delivery system is advanced to the target treatment site, and if optional pillowing is used as described herein, the stent edges are protected by the pillowing, 752. Pillowing may protect the proximal, distal or intermediate edges of the stent during proximal advancement through a blood vessel or an introducer or sheath. Pillowing may also protect the proximal, distal, or intermediate edges of the stent during distal retraction through a blood vessel or a sheath or introducer. Pillowing may also protect and prevent unwanted scraping or removal of a therapeutic agent carried by the mother stent, daughter stent, or any stent or any coatings disposed on any of the stent or stents. Pillowing may be included on the mother stent, an optional daughter stent, or on both mother and daughter stents. The mother stent is aligned with the mother vessel treatment site. Optional repositioning may be needed 754. Pillowing protects the stent edges and coatings or therapeutic agents carried by the stent during repositioning. The daughter balloon may be partially expanded or the mother balloon may be partially expanded to allow relative movement of the daughter catheter relative to the mother catheter, 756. The daughter catheter is aligned with the daughter vessel treatment area, 758. Optional pillowing protects the stent edges or any therapeutic agents or coatings carried by the stent or stents during optional repositioning. Once the mother and daughter catheters are properly positioned at the treatment site, the mother balloon may be fully inflated to radially expand the mother stent into the mother vessel, 760. If the daughter catheter includes a daughter stent, the daughter balloon may be fully expanded to expand the daughter stent into the daughter vessel, 762. Optionally kissing balloons may be used where both mother and daughter balloons are simultaneously inflated to tack both stents into position and ensure even radial expansion of the stent or stents, 764. The stent delivery catheter may be removed from the patient when the procedure complete, 766.

FIGS. 8A-8C, 8C1, and 8D-8H illustrate a method for manufacturing a fully crimped stent delivery system with pillowed expandable members, such as the system described above in FIG. 7.

Figures 8A, 8B:
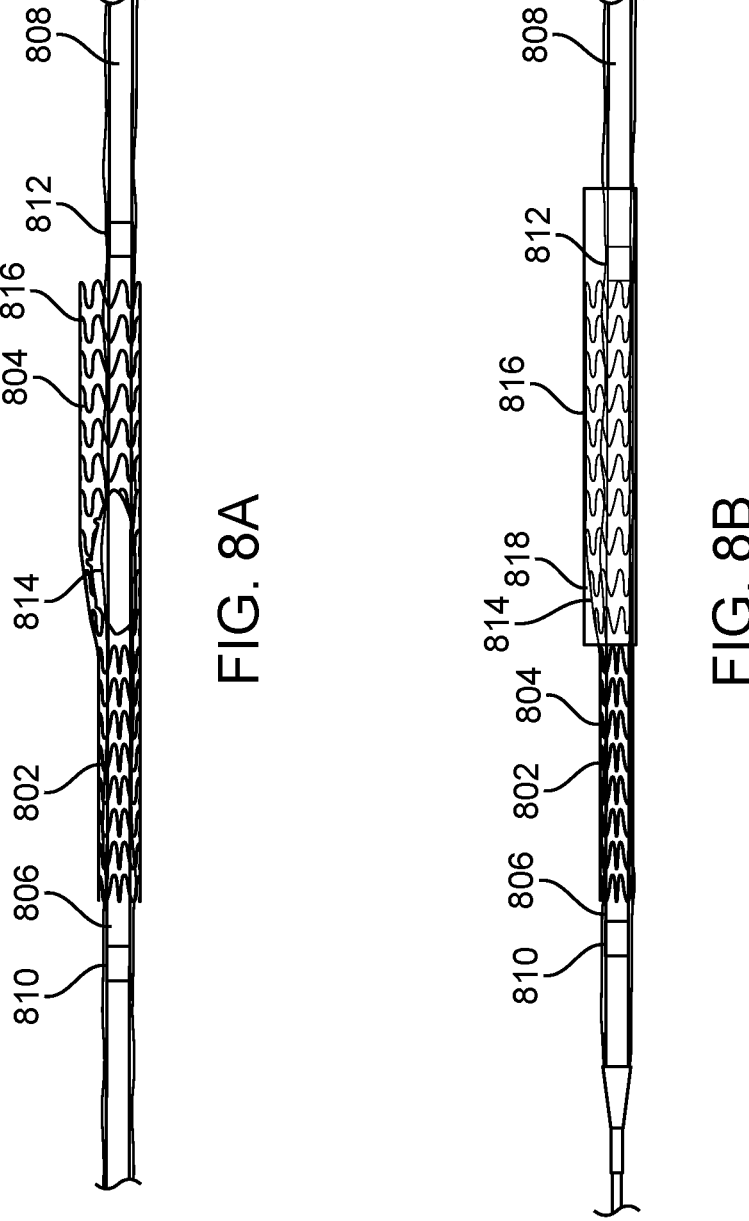

FIG. 8A shows pre-crimping of a distal portion 802 of the mother stent 804 disposed over a mother balloon 806 on the distal end of the mother elongate shaft 808. The stent 804 is disposed adjacent the proximal and distal radiopaque marker bands 810, 812 on the elongate shaft 808 in order to mark the proximal and distal ends of the mother stent 804 which also mark the proximal and distal ends of the working length of the balloon. Here, the partial crimp is a loose crimp made with the fingers or a crimping tool or crimping fixture (e.g. collapsible iris) in order to crimp the mother stent to the mother balloon enough to prevent it from easily dislodging during processing but not necessarily with enough retention force to remain in place during use (e.g. delivery through a blood vessel). The stent distal 802 of the side hole 814 is partially crimped to the mother balloon 806. The proximal portion 816 of the stent 804 proximal of the side hole 814 remains uncrimped. The side hole 814 remains uncrimped or may be partially crimped.

FIG. 8B shows the distal portion 802 of the mother stent 804 fully crimped to the mother balloon 806. Here, a constraining sheath 818 is disposed over the stent 804 to cover the side hole 814 and proximal portion 816 of the stent 804. The distal portion 802 of the stent 804 is then disposed in a crimping tool or crimping machine (not illustrated) and fully crimped to the balloon. A full crimp prevents the stent from axially moving along the mother elongate balloon 806 during delivery of the catheter through a blood vessel. As previously discussed, heat and pressure may be applied to the balloon 806 and stent 804 to allow the balloon to pillow up into the apertures of the stent 804 thereby increasing stent retention after crimping.

Figures 8C, 8D:
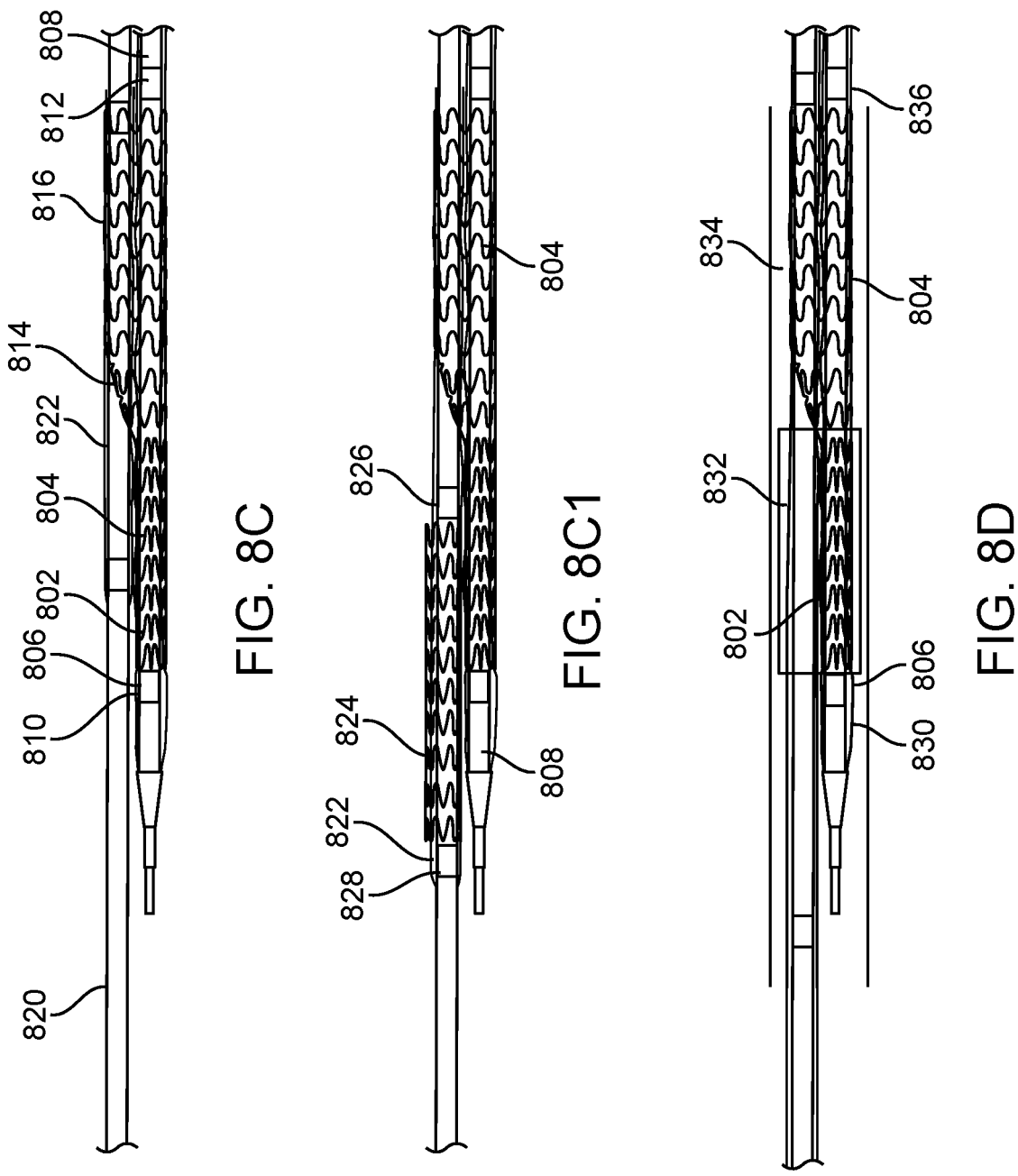

FIG. 8C shows the daughter catheter 820 with a daughter balloon 822 slidably advanced under the proximal end 816 of the mother stent 804 and out the side hole 814. The proximal end 816 of the stent 804 remains uncrimped to allow the daughter catheter 820 to be slidably advanced under the stent 804. Optionally the daughter catheter 820 may include a daughter stent (seen in FIG. 8C1) fully crimped over the daughter balloon 822 but this will be omitted in this example for ease of illustration and discussion.

FIG. 8C1 is substantially the same as FIG. 8C but in this example, an optional daughter stent 824 is fully crimped (e.g. the stent will not slide or otherwise move relative to the daughter balloon 822 during use such as delivery through a blood vessel) to the daughter balloon 822. The daughter stent 824 may be any length, but in some examples may be approximately half the length of the mother stent 804. The daughter stent 824 is disposed between proximal and distal radiopaque markers 826, 828 on the daughter catheter 820 to mark the ends of the stent 824. The daughter stent 824 may be distal of the mother stent 804 with little or no overlap between the two stents so that profile of the device is minimized during delivery. Other aspects of the mother catheter with elongate shaft 808 and mother stent 804 are generally the same as previously disclosed above in FIGS. 8A-8C.

FIG. 8D shows formation of a distal pillowed region 830 on the mother balloon 806 disposed under mother stent 804. Here, a first sheath 832 such as a polyimide tube is disposed over the distal crimped stent portion 802 to prevent it from expanding when pressurized and heated. A second sheath 834 having a larger inner diameter is disposed over the entire mother stent 804 and mother balloon 806 (or at a minimum over the distal region 830 to be pillowed and proximal region 836 to be pillowed) to allow the mother balloon 806 slightly to expand when inflated under pressure and heat to form the proximal and distal pillowed regions on the mother balloon.

Figures 8E, 8F:
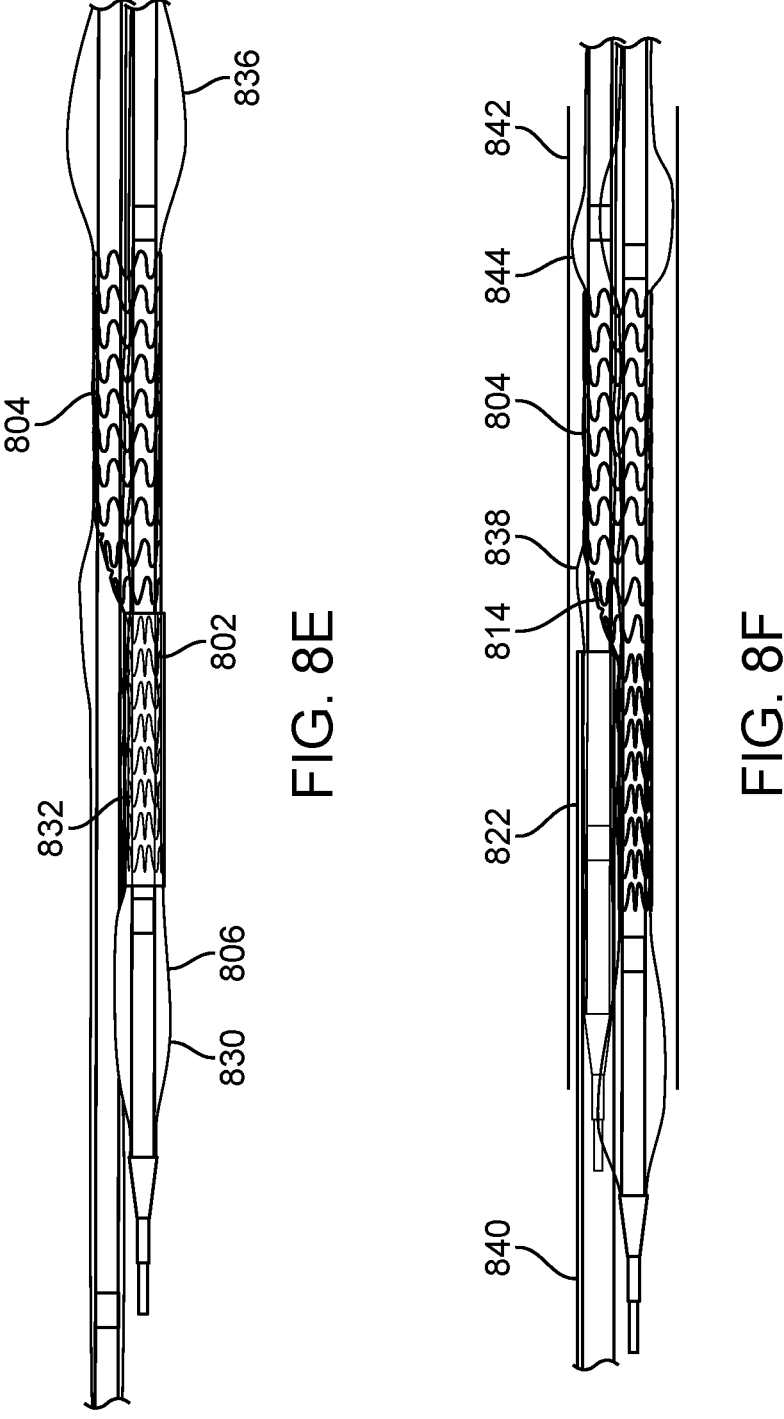

FIG. 8E shows the second sheath removed from FIG. 8D with proximal and distal pillowing 836, 830 on the mother balloon 806. The inner most sheath 832 remains disposed over the distal crimped region 802 of the mother stent 804. The proximal and distal ends of the daughter balloon uncovered by mother stent 804 remain relatively flat and non-protruding until optional pillows on the daughter balloon are formed next.

FIG. 8F shows formation of the daughter balloon pillowed region 838 adjacent the side hole 814 of the mother stent 804. Here an inner sheath 840 is disposed over the daughter balloon 822 to tightly fit over the distal portion of the daughter balloon to maintain the original balloon pleat and folds and constrain the balloon 822 from expanding during inflation under heat and pressure. The inner sheath 840 does not cover a portion 838 (the region to be pillowed) of the daughter balloon 822 closest to the side hole 814 of the mother stent 804. A second larger diameter sheath 842 is disposed over the inner sheath 840 and the center or intermediate portion of the daughter balloon 822 is allowed to expand slightly during inflation under heat and pressure which forms the pillowed region 838 adjacent the edges of the side hole 814 in the stent. The proximal portion 844 of the daughter balloon 822 may slightly pillow or remain substantially flat.

Figures 8G, 8H:
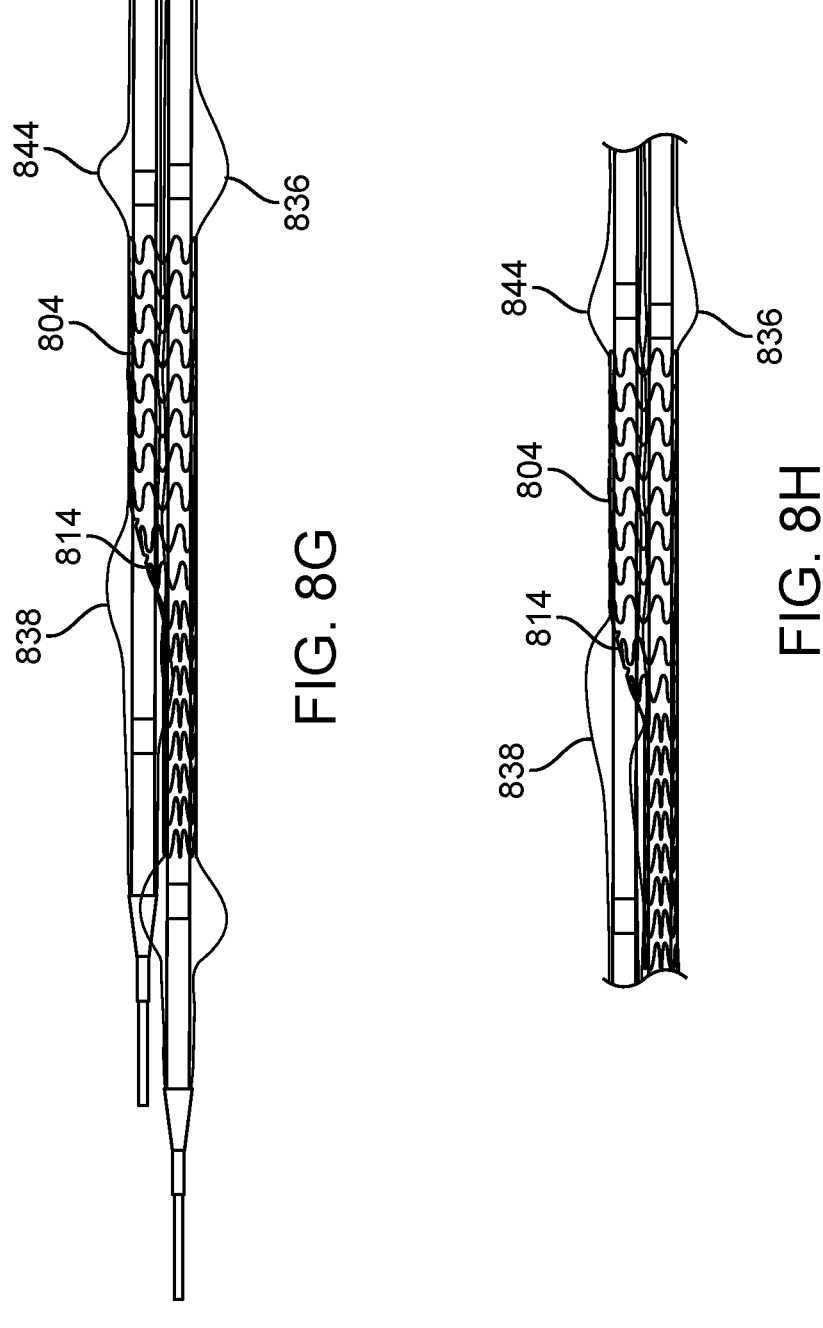

FIGS. 8G and 8H illustrate the pillowing 838 in the daughter balloon created around the side hole 814 of the mother stent 804 in FIG. 8F above and also the proximal pillowing 836, 844 of the mother and daughter balloons formed in FIG. 8D. The sheaths have been removed and the pillowed daughter balloon near the side hole and the proximally pillowed mother and daughter balloons are also visible. The pillowed regions form a raised layer of balloon material that provides a protective barrier adjacent the respective stent edges to prevent the stent edges from catching on other surfaces which can bend, deform or eject the stent from the balloon(s). The pillowed edges also help prevent therapeutic agents carried by the mother or daughter stents or any coatings disposed thereon from being scraped or otherwise damaged.

FIGS. 8G and 8H also show that after formation of the intermediate pillowed region 838, the proximal portion of the mother stent (the region proximal of the side hole) may be fully crimped to both the mother and daughter balloons by placing it in a crimping tool or a crimping machine where the stent is compressed onto both the mother and daughter proximal balloons. A sheath (not illustrated) may be disposed over a proximal portion of the mother stent to constrain it and prevent it from expanding during the crimping process where the stent is crimped onto the mother and daughter balloons while the balloons are partially inflated under heat and pressure. FIG. 8H shows a close-up of the intermediate and proximal ends of the mother stent.

FIGS. 8A-8H highlight fabrication of a stent delivery system with a mother stent only. One of skill in the art will appreciate that if an optional daughter stent is crimped over the daughter balloon, the daughter stent will be fully crimped to the daughter stent so that it does not move during use (e.g. delivery through a vessel). Formation of the pillows around the daughter stent is substantially the same as previously described above with the exception that the daughter stent may be covered with a constraining sheath to prevent unwanted expansion of the daughter stent during pillow formation under pressure and heat application.

Additionally, one of skill in the art will appreciate that any one or combination of stents (e.g. mother stent, daughter stent), any combination of balloons (e.g. mother balloon, daughter balloon), and any combination of pillowing (e.g. proximal mother balloon pillowing, distal mother balloon pillowing, pillowing of the mother balloon around the mother stent side hole, proximal daughter balloon pillowing, distal daughter balloon pillowing, pillowing of the daughter balloon around the mother stent side hole, etc.) may be used in any stent delivery system describe herein.

NOTES AND EXAMPLES

The following, non-limiting examples, detail certain aspects of the present subject matter to solve the challenges and provide the benefits discussed herein, among others.

Example 1 is a stent delivery system for treating a bifurcated vessel, the system comprising: a first elongate shaft having a proximal end, a distal end, and a first expandable member coupled to the distal end of the first elongate shaft; a first stent having a proximal end, a distal end, and a sidewall with a side hole disposed therethrough, the side hole disposed between the proximal end and the distal end of the first stent, the first stent disposed over the first expandable member; and a second elongate shaft having a proximal end, a distal end, and a second expandable member coupled to the distal end of the second elongate shaft, wherein the second elongate shaft is slidably disposed under the proximal end of the first stent and extends out of the side hole, wherein the first stent is fully crimped over a proximal portion and a distal portion of the first expandable member and a proximal portion of the second expandable member so as to prevent axial movement of the first stent along the first elongate shaft or the second elongate shaft during delivery.

Example 2 is the system of Example 1, wherein a distal portion of the first expandable member is pillowed to provide a protective barrier that protects a distal edge of the first stent.

Example 3 is the system of any of Examples 1-2, wherein a proximal portion of the first expandable member is pillowed to provide a protective barrier that protects a proximal edge of the first stent.

Example 4 is the system of any of Examples 1-3, wherein a proximal portion of the second expandable member is pillowed to provide a protective barrier that protects a proximal edge of the first stent.

Example 5 is the system of any of Examples 1-4, wherein an intermediate portion of the first expandable member is disposed between the proximal and distal ends thereof, and is pillowed to provide a protective barrier that protects an edge of the side hole.

Example 6 is the system of any of Examples 1-5, wherein an intermediate portion of the second expandable member is disposed between the proximal and distal ends thereof, and is pillowed to provide a protective barrier that protects an edge of the side hole.

Example 7 is the system of any of Examples 1-6, wherein expansion of the second expandable member radially expands the proximal portion of the first stent thereby allowing the second elongate shaft to slide relative to the first elongate member, while the first stent remains fully crimped to the first expandable member so that the stent does not axially move relative to the first elongate shaft during delivery.

Example 8 is the system of any of Examples 1-7, wherein expansion of the first expandable member radially expands the first stent thereby allowing axial movement of the first and second elongate shafts relative to the first stent.

Example 9 is the system of any of Examples 1-8, further comprising a second stent disposed over the second expandable member, wherein the second stent is fully crimped to the second expandable member thereby preventing axial movement of the second stent relative to the second elongate shaft during delivery thereof.

Example 10 is a stent delivery system for treating a bifurcated vessel, the system comprising: a first elongate shaft having a proximal end, a distal end, and a first expandable member coupled to the distal end of the first elongate shaft; a first stent having a proximal end and a distal end, and a sidewall with a side hole disposed therethrough, the side hole disposed between the proximal end and the distal end of the first stent, the first stent disposed over the first expandable member; and a second elongate shaft having a proximal end, a distal end, and a second expandable member coupled to the distal end of the second elongate shaft, wherein the second elongate shaft is slidably disposed under the proximal end of the first stent and extends out of the side hole, wherein the first stent is fully crimped over a proximal portion and a distal portion of the first expandable member and a proximal portion of the second expandable member so as to prevent axial movement of the first stent along the first elongate shaft or the second elongate shaft during delivery, wherein a distal portion of the first expandable member is pillowed to provide a protective barrier that protects a distal edge of the first stent, wherein a proximal portion of the first expandable member is pillowed to provide a protective barrier that protects a proximal edge of the first stent, and wherein a proximal portion of the second expandable member is pillowed to provide a protective barrier that protects a proximal edge of the first stent.

Example 11 is the system of Example 10, wherein an intermediate portion of the first expandable member disposed between the proximal and distal ends thereof is pillowed to provide a protective barrier that protects an edge of the side hole.

Example 12 is the system of any of Examples 10-11, wherein an intermediate portion of the second expandable member disposed between the proximal and distal ends thereof is pillowed to provide a protective barrier that protects an edge of the side hole.

Example 13 is the system of any of Examples 10-12, wherein expansion of the second expandable member radially expands the proximal portion of the first stent thereby allowing the second elongate shaft to slide relative to the first elongate member, while the first stent remains fully crimped to the first expandable member so that the first stent does not axially move relative to the first elongate shaft during delivery.

Example 14 is the system of any of Examples 10-13, wherein expansion of the first expandable member radially expands the first stent thereby allowing axial movement of the first and second elongate shafts relative to the first stent.

Example 15 is the system of any of Examples 10-14, further comprising a second stent disposed over the second expandable member, wherein the second stent is fully crimped to the second expandable member thereby preventing axially movement of the second stent relative to the second elongate shaft during delivery thereof.

Example 16 is a method for treating a bifurcated vessel, the method comprising: providing a stent delivery system comprising a first elongate shaft having a first expandable member, a first stent disposed over the first expandable member, and a second elongate shaft having a second expandable member; advancing the stent delivery system through a blood vessel toward the bifurcated vessel, wherein the first stent is fully crimped to both the first and second expandable members and remains disposed over the first and second expandable members without movement of the first stent relative to the first or second elongate shafts during the advancement; radially expanding the second expandable member to expand a proximal portion of the first stent and allowing axial movement of the second elongate shaft relative to the first elongate shaft, while the first stent remains coupled to the first expandable member without relative movement therebetween during the advancement; axially sliding the second elongate shaft under the first stent and through a side hole in the first stent to dispose the second expandable member into a desired position; and radially expanding the first expandable member to expand the first stent into engagement with a treatment area in the bifurcated vessel.

Example 17 is the method of Example 16, wherein advancing the stent delivery system comprises protecting a distal edge of the first stent with a pillowed distal region of the first expandable member that provides a protective barrier in front of the distal edge of the first stent.

Example 18 is the method of any of Examples 16-17, wherein advancing the stent delivery system comprises protecting an edge of the side hole with a pillowed intermediate region of the first expandable member or the second expandable member, the pillowed intermediate region disposed between a proximal end and a distal end of the respective first or second expandable member, the pillowed region providing a protective barrier in front of the edge of the side hole of the first stent.

Example 19 is the method of any of Examples 16-18, wherein advancing the stent delivery system comprises protecting a proximal edge of the first stent with a pillowed proximal region of the first expandable member or the second expandable member, the pillowed region providing a protective barrier in front of the proximal edge of the first stent.

Example 20 is the method of any of Examples 16-19, further comprising radially expanding a second stent into a target treatment region of the bifurcated vessel, the second stent disposed over the second expandable member and fully crimped thereto prior to radial expansion of the second stent.

Example 21 is a method of manufacturing a stent delivery system for treating a bifurcation, the method comprising fully crimping a distal portion of a first stent onto a first expandable member; inserting a second expandable member under a proximal end of the first stent and out a side hole in a side wall of the first stent; forming a proximal pillowed region and distal pillowed region on the first expandable member that protects a respective proximal or distal edge of the first stent; forming an intermediate pillowed region on the second expandable member that protects an edge of the side hole of the first stent; and fully crimping a proximal portion of the first stent to the first and second expandable members.

Example 22 is the method of Example 21, further comprising partially crimping the distal portion of a first stent to the first expandable member prior to fully crimping the first stent thereto.

Example 23 is the method of any of Examples 21-22, further comprising centering the first stent over the first expandable member prior to the partial crimping.

Example 24 is the method of any of Examples 21-23, wherein forming the proximal or the distal pillowed region comprises expanding the first expandable member under heat and pressure.

Example 25 is the method of any of Examples 21-24, wherein forming the intermediate pillowed region comprises expanding the second expandable member under heat and pressure.

In Example 26, the apparatuses or method of any one or any combination of Examples 1-25 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A stent delivery system for treating a bifurcated vessel, the system comprising:

a first elongate shaft having a proximal end, a distal end, and a first expandable member coupled to the distal end of the first elongate shaft;

a first stent having a proximal end, a distal end, and a sidewall with a side hole disposed therethrough, the side hole disposed between the proximal end and the distal end of the first stent, the first stent disposed over the first expandable member; and a second elongate shaft having a proximal end, a distal end, and a second expandable member coupled to the distal end of the second elongate shaft, wherein the second elongate shaft is slidably disposed under the proximal end of the first stent and extends out of the side hole, wherein the first stent is fully crimped over a proximal portion and a distal portion of the first expandable member and a proximal portion of the second expandable member so as to prevent axial movement of the first stent along the first elongate shaft or the second elongate shaft during delivery, wherein a distal portion of the first expandable member is pillowed to form an enlarged distal dumbbell having a diameter greater than a diameter of a distal-most edge of the first stent, the enlarged distal dumbbell providing a protective barrier that protects the distal-most edge of the first stent, wherein a proximal portion of the first expandable member is pillowed to form an enlarged proximal dumbbell having a diameter greater than a diameter of a proximal-most edge of the first stent, the enlarged proximal dumbbell providing a protective barrier that protects the proximal-most edge of the first stent, wherein the second elongate shaft is axially slidable under the first stent and through the side hole disposed between the proximal end and the distal end of the first stent during a relative axial movement between the first and second elongate shafts, wherein an intermediate portion of the second expandable member is disposed between the proximal and distal ends thereof, and the intermediate portion is pillowed to form a circumferential raised barrier adjacent to an edge of the side hole, and wherein the raised barrier provides protection preventing the edge of the side hole from catching on surrounding tissue or an edge of an introducer sheath during delivery.

2. The system of claim 1, wherein expansion of the second expandable member radially expands the proximal portion of the first stent thereby allowing the second elongate shaft to slide relative to the first elongate shaft, while the first stent remains fully crimped to the first expandable member so that the stent does not axially move relative to the first elongate shaft during delivery.

3. The system of claim 1, wherein expansion of the first expandable member radially expands the first stent thereby allowing axial movement of the first and second elongate shafts relative to the first stent.

4. The system of claim 1, further comprising a second stent disposed over the second expandable member, wherein the second stent is fully crimped to the second expandable member thereby preventing axial movement of the second stent relative to the second elongate shaft during delivery thereof.

5. The system of claim 1, wherein the second expandable member is configured to be partially expanded to create a gap between the proximal end of the first stent and the second elongate shaft to allow the second elongate shaft to axially slide under the first stent.

6. A stent delivery system for treating a bifurcated vessel, the system comprising:

a first elongate shaft having a proximal end, a distal end, and a first expandable member coupled to the distal end of the first elongate shaft;

a first stent having a proximal end and a distal end, and a sidewall with a side hole disposed therethrough, the side hole disposed between the proximal end and the distal end of the first stent, the first stent disposed over the first expandable member; and a second elongate shaft having a proximal end, a distal end, and a second expandable member coupled to the distal end of the second elongate shaft, wherein the second elongate shaft is slidably disposed under the proximal end of the first stent and extends out of the side hole, wherein the first stent is fully crimped over a proximal portion and a distal portion of the first expandable member and a proximal portion of the second expandable member so as to prevent axial movement of the first stent along the first elongate shaft or the second elongate shaft during delivery, wherein a distal portion of the first expandable member is pillowed to form an enlarged distal dumbbell having a diameter greater than a diameter of a distal-most edge of the first stent, the enlarged distal dumbbell providing a protective barrier that protects the distal-most edge of the first stent, wherein a proximal portion of the first expandable member is pillowed to form an enlarged proximal dumbbell having a diameter greater than a diameter of a proximal-most edge of the first stent, the enlarged proximal dumbbell providing a protective barrier that protects the proximal-most edge of the first stent, and wherein a proximal portion of the second expandable member is pillowed to provide a protective barrier that protects a proximal edge of the first stent, wherein the second elongate shaft is axially slidable under the first stent and through the side hole disposed between the proximal end and the distal end of the first stent during a relative axial movement between the first and second elongate shafts, wherein an intermediate portion of the second expandable member is disposed between the proximal and distal ends thereof, and the intermediate portion is pillowed to form a circumferential raised barrier adjacent to an edge of the side hole, and wherein the raised barrier provides protection preventing the edge of the side hole from catching on surrounding tissue or an edge of an introducer sheath during delivery.

7. The system of claim 6, wherein expansion of the second expandable member radially expands the proximal portion of the first stent thereby allowing the second elongate shaft to slide relative to the first elongate shaft, while the first stent remains fully crimped to the first expandable member so that the first stent does not axially move relative to the first elongate shaft during delivery.

8. The system of claim 6, wherein expansion of the first expandable member radially expands the first stent thereby allowing axial movement of the first and second elongate shafts relative to the first stent.

9. The system of claim 6, further comprising a second stent disposed over the second expandable member, wherein the second stent is fully crimped to the second expandable member thereby preventing axially movement of the second stent relative to the second elongate shaft during delivery thereof.

10. The system of claim 6, wherein the second expandable member is configured to be partially expanded to create a gap between the proximal end of the first stent and the second elongate shaft to allow the second elongate shaft to axially slide under the first stent.

* * * * *